US012698474B2

(12) United States Patent　(10) Patent No.: US 12,698,474 B2
Jung　(45) Date of Patent: *Aug. 4, 2026

(54) B-CELL CULTIVATION METHOD

(71) Applicant: Hoffmann-La Roche Inc., Little Falls, NJ (US)

(72) Inventor: Friederike Jung, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 915 days.

This patent is subject to a terminal disclaimer.

(21) Appl. No.: 16/455,681

(22) Filed: Jun. 27, 2019

(65) Prior Publication Data

US 2020/0149006 A1　May 14, 2020

Related U.S. Application Data

(63) Continuation of application No. PCT/EP2017/084305, filed on Dec. 22, 2017.

(30) Foreign Application Priority Data

Jan. 2, 2017　(EP) ..................................... 17150040
Mar. 27, 2017　(EP) ..................................... 17162948

(51) Int. Cl.
　*C12N 5/0781*　(2010.01)
　*C12P 21/00*　(2006.01)
(52) U.S. Cl.
　CPC ............ *C12N 5/0635* (2013.01); *C12P 21/00* (2013.01); *C12N 2501/2301* (2013.01); *C12N 2501/2302* (2013.01); *C12N 2501/2306* (2013.01); *C12N 2501/231* (2013.01); *C12N 2501/25* (2013.01); *C12N 2501/999* (2013.01); *C12N 2502/1107* (2013.01); *C12N 2502/70* (2013.01)
(58) Field of Classification Search
　CPC .......... C12N 5/0635; C12N 2501/2301; C12N 2501/2302; C12N 2501/2306; C12N 2501/231; C12N 2501/25; C12N 2502/1107; C12P 21/00
　See application file for complete search history.

(56) References Cited

U.S. PATENT DOCUMENTS

| | | | |
|---|---|---|---|
| 5,010,182 A | 4/1991 | Brake et al. | |
| 5,637,677 A | 6/1997 | Greene et al. | |
| 7,807,415 B2 | 10/2010 | Groen et al. | |
| 2006/0051348 A1 | 3/2006 | Gorlach | |
| 2007/0269868 A1 | 11/2007 | Jensen et al. | |
| 2013/0084637 A1* | 4/2013 | Endl | C07K 16/00 |
| | | | 435/325 |
| 2013/0115674 A1* | 5/2013 | Sutkowski | C07K 16/3015 |
| | | | 435/375 |
| 2013/0177987 A1 | 7/2013 | Schram et al. | |

FOREIGN PATENT DOCUMENTS

| | | | |
|---|---|---|---|
| EP | 0362179 A2 | 4/1990 |
| EP | 0362179 A3 | 4/1990 |
| EP | 0488470 A1 | 6/1992 |
| EP | 1860181 A1 | 11/2007 |
| WO | 1999/42077 A2 | 8/1999 |
| WO | 2008/045140 A1 | 4/2008 |
| WO | 2008/144763 A2 | 11/2008 |
| WO | 2011/147903 A1 | 12/2011 |
| WO | 2013/076139 A1 | 5/2013 |
| WO | 2013/092716 A1 | 6/2013 |
| WO | 2015/000624 A1 | 1/2015 |

OTHER PUBLICATIONS

Yanaba et al. The Development and Function of Regulatory B Cells Expressing IL-10 (B10 cells) Requires Antigen Receptor Diversity and TLR Signals. J Immunol. Jun. 15, 2009; 182(12): 7459-7472 (Year: 2009).*
Lagoo et al. Interleukin 2 Produced By Activated B Lymphocytes Acts as an Autocrine Proliferation-Inducing Lymphokine. Cytokine, vol. 2, No. 4 Jul. 1990: pp. 272-279 (Year: 1990).*
Ruff et al. PMA-activation of peripheral blood and tonsillar B lymphocytes induces large adhesive cells reminiscent of large extrafollicular (monocytoid) B cells. Virchows Archiv (1994) 424:195-204 (Year: 1994).*
Goldfeld et al. Human Tumor Necrosis Factor a Gene Regulation in Phorbol Ester Stimulated T and B Cell Lines. J. Exp. Med. vol. 174 Jul. 1991 73-81 (Year: 1991).*
Unit Conversion Table. downloaded from www.rndsystems.com/resources/technical-information/unit-conversion-table. p. 1-3 (Year: 2023).*
Armitage et al. 11-15 Has Stimulatory Activity for the Induction of B Cell Proliferation and Differentiation. The Journal of Immunology , 1995, 154: 483-490. (Year: 1995).*
Bertoglio. Monocyte-Independent Stimulation of Human B Lymphocytes By Phorbol Myristate Acetate. The Journal of Immunology, 1983, 131: 2279-2281. (Year: 1983).*
Reparon-Schuijt et al. Presence of a Population of CD201, CD382 B Lymphocytes With Defective Proliferative Responsiveness in the Synovial Compartment of Patients With Rheumatoid Arthritis. Arthritis & Rheumatism vol. 44, No. 9, Sep. 2001, pp. 2029-2037 (Year: 2001).*
Muraguchi et al. The Essential Role of B Cell Stimulatory Factor 2 (BSF-2/IL-6) for the Terminal Differentiation of B Cells. J. Exp. MED. vol. 167 Feb. 1988; 332-344 (Year: 1988).*
Jelinek et al. Role of IL-12 in Human B Lymphocyte Proliferation and Differentiation. The journal of Immunology, 1995, 154: 1606-1613 (Year: 1995).*
Bovia, Fabrice, et al., "Efficient transduction of primary human B lymphocytes and nondividing myeloma B cells with HIV-1-derived lentiviral vectors" Blood 101(5):1727-1733 (Oct. 7, 2002).
Clackson et al., "Making antibody fragments using phage display libraries" Nature 352(6336):624-628 (Aug. 15, 1991).
Ghamlouch, H., et al., "Phorbol myristate acetate, but not CD4OL, induces the differentiation of CLL B cells into Ab-secreting cells" Nat Immunol Cell Bio 92(7):591-604 (Aug. 1, 2014).

(Continued)

*Primary Examiner* — Taeyoon Kim

(57) ABSTRACT

Herein is reported a method for co-cultivating B-cells in the presence of phorbol myristate acetate, IL-1beta, TNFalpha, IL-2, IL-10 and IL-6.

13 Claims, No Drawings

(56) References Cited

OTHER PUBLICATIONS

Hausherr, A., et al., "Inhibition of IL-6-dependent growth of myeloma cells by an acidic peptide repressing the gp130-mediated activation of Src family kinases" Oncogene 26:4987-4998 (Feb. 19, 2007).

Imlach, Wendy, et al., "Orf virus-encoded interleukin-10 stimulates the proliferation of murine mast cells and inhibits cytokine synthesis in murine peritoneal macrophages" J Gen Virol 83:1049-1058 (Jan. 1, 2002).

International Preliminary Report on Patentability—PCT/EP2017/084305:pp. 1-9 (Jul. 11, 2019).

"International Search Report—PCT/EP2017/084305":pp. 1-6 (Feb. 13, 2018).

Jensen, James B., et al., "Tumor Necrosis Factor Does Not Induce Plasmodium falciparum Crisis Forms" Infect Immun 55(7):1722-1724 (Mar. 17, 1987).

Kindt et al. Kuby Immunol Sixth edition, New York:W. H. Freeman and Company,:91 (2007).

Kwekkeboom et al., "An efficient procedure for the generation of human monoclonal antibodies based on activation of human B lymphocytes by a murine thymoma cell line" J Immunol Meth 160(1):117-127 (Jan. 1, 1993).

Manfredini, R., et al., "Development of an IL-6 antagonist peptide that induces apoptosis in 7TD1 cells" Peptides 24:1207-1220 (Apr. 14, 2003).

Mannel et al. et al., "Macrophages as a Source of Tumoricidal Activity (Tumor-Necrotizing Factor)" Infect Immun 30(2):523-530 ( 1980).

Masri et al., "Cloning and expression in *E. coli* of a functional Fab fragment obtained from single human lymphocyte against anthrax toxin" Molec Immunol 44:2101-2106 ( 2007).

Morgan et al., "Antibody-Induced Down-Regulation of a Mutated Insulin Receptor Lacking an Intact Cytoplasmic Domain" Biochemistry 26(11):2959-2963 (Jun. 2, 1987).

Orencole, Scott F., et al., "Characterization of a Subclone (D10S) of the D10.G4.1 Helper T-CELL Line which Proliferates to Attomolar Concentrations of Interleukin-1 in the Absence of Mitogens" Cytokine 1(1):14-22 (Nov. 1, 1989).

Pak et al., "Super-CHO—A cell line capable of autocrine growth under fully defined protein-free conditions" Cytotechnology 22:139-146 ( 1996).

Paus et al., "Antigen recognition strength regulates the choice between extrafollicular plasma cell and germinal center B cell differentiation" J Exp Med 203(4):1081-1091 (Apr. 2006).

Portolano et al., "Lack of promiscuity in autoantigen-specific H and L chain combinations as revealed by human H and L chanin 'Roulette'" J Immunol 150(3):880-887 (Feb. 1, 1993).

Ruff MR and Gifford GE et al., "Rabbit tumor necrosis factor: mechanism of action" Infect Immun 31(1):380-385 (Jan. 1981).

Sambrook et al. Molecular Cloning 2nd edition, Cold Spring Harbor Laboratory Press, ( 1989).

Schroeder, Jr., H. et al., "Structure and evolution of mammalian VH families" Int Immunol 2(1):41-50 (Sep. 19, 1989).

Smith et al., "The extent of affinity maturation differs between the memory and antibody-forming cell compartments in the primary immune response" EMBO J 16(11):2996-3006 ( 1997).

Symons, J.A. et al. Lymphokines and Interferons : A Practical Approach Clemens, M.J., Oxford, England:Oxford University Press,:272 (Sep. 1, 1987).

Thompson-Snipes, L., et al., "Interleukin 10: A Novel Stimulatory Factor for Mast Cells and Their Progenitors" J Exp Med 173:507-510 (Feb. 1, 1991).

Tucci et al., "Effects of Eleven Cytokines and OF IL-1 and Tumor Necrosis Factor Inhibitors in a Human B Cell Assay" J Immunol 148(9):2778-2784 (May 1, 1992).

Van Snick, J., et al., "Purification and NH2-terminal amino acid sequence of a T-cell-derived lymphokine with growth factor activity for B-cell hybridomas" PNAS 83:9679-9683 (Sep. 2, 1986).

Wadhwa, Meenu, et al., "The 2nd International standard for Interleukin-2 (IL-2) Report of a collaborative study" J Immunol Methods 397:1-7 (Aug. 13, 2013).

Weber et al., "Combining EL4-B5-based B-cell stimulation and phage display technology for the successful isolation of human anti-Scl-70 autoantibody fragments" J Immunol Meth 278:249-259 ( 2003).

Weitkamp et al., "Generation of recombinant human monoclonal antibodies to rotavirus from single antigen-specific B cells selected with fluorescent virus-like particles" J Immunol Meth 275:223-237 ( 2003).

Werner-Favre, C., et al., "IgG subclass switch capacity is low in switched and in IgM-only, but high in IgD+IgM+, postgerminal center (CD27+) human B cells" Eur J Immunol 31:243-249 (Oct. 26, 2000).

Weston, L., et al., "A convenient and reliable IL-2 bioassay using frozen CTLL-2 to improve the detection of helper T lymphocyte precursors" Immunol Cell Bio 76:190-192 (Nov. 12, 1997).

Wrammert et al., "Rapid cloning of high-affinity human monoclonal antibodies against influenza virus" Nature 453:667-672 (May 2008).

Zubler et al., "Activated B cells express Receptors for, and proliferate in response to, pure Interleukin 2" J Exp Med 160:1170-1183 (Oct. 1984).

Zubler, "Polyclonal B cell responses in the presence of defined filler cells: complementary effects of lipopolysaccharide and anti-immunoglobulin antibodies" Eur J Immunol 14:357-363 ( 1984).

* cited by examiner

B-CELL CULTIVATION METHOD

CROSS REFERENCE TO RELATED APPLICATIONS

This application is continuation of International Application No. PCT/EP2017/084305, filed Dec. 22, 2017, which claims priority from European Patent Application No. 17150040.8, filed Jan. 2, 2017, and European Patent Application No. 17162948.8, filed Mar. 27, 2017. The contents of each of foregoing applications are incorporated herein by reference in their entireties.

Herein are reported methods for co-cultivating B-cells with feeder cells, wherein a fully defined synthetic feeder mix is applied. The method can be used, e.g., for obtaining the amino acid sequence of at least the variable domains of a monoclonal antibody secreted by the co-cultivated B-cell, and for producing the antibody.

BACKGROUND OF THE INVENTION

For obtaining cells secreting monoclonal antibodies the hybridoma technology developed by Koehler and Milstein is widely used. But in the hybridoma technology only a fraction of the B-cells obtained from an immunized experimental animal can be fused and propagated. The source of the B-cells is generally an organ of an immunized experimental animal such as the spleen.

Zubler et al. started in 1984 to develop a different approach for obtaining cells secreting monoclonal antibodies (see e.g. Eur. J. Immunol. 14 (1984) 357-63, J. Exp. Med. 160 (1984) 1170-1183). Therein the B-cells are obtained from the blood of the immunized experimental animal and co-cultivated with murine EL-4 B5 feeder cells in the presence of a cytokine comprising feeder mix. With this methodology up to 50 ng/ml antibody can be obtained after 10-12 days of co-cultivation.

Kwekkeboom, J., et al. (J. Immunol. Meth. 160 (1993) 117-127) reported an efficient procedure for the generation of human monoclonal antibodies based on activation of human B lymphocytes by a murine thymoma cell line. They reported that for human B-cells the cultivation conditions should be with irradiated EL4B5 in the presence of PMA (5 ng/ml) plus 5% T cells supernatant.

Weitkamp, J-H., et al., (J. Immunol. Meth. 275 (2003) 223-237) report the generation of recombinant human monoclonal antibodies to rotavirus from single antigen-specific B-cells selected with fluorescent virus-like particles.

Weber, M., et al. (J. Immunol. Meth. 278 (2003) 249-259) reported combining EL4-B5-based B-cell stimulation and phage display technology for the successful isolation of human anti-Scl-70 autoantibody fragments. The cell mixture was incubated at 37° C. in RPMI 1640 medium supplemented with 10% FCS, 3% macrophage/T-cell culture supernatant, nonessential amino acids, and 3 ng/ml phorbol myristate acetate.

A method of producing a plurality of isolated antibodies to a plurality of cognate antigens is reported in US 2006/0051348.

In WO 2008/144763 and WO 2008/045140 antibodies to IL-6 and uses thereof and a culture method for obtaining a clonal population of antigen-specific B cells are reported, respectively.

A culture method for obtaining a clonal population of antigen-specific B-cells is reported in US 2007/0269868.

Masri et al. (in Mol. Immunol. 44 (2007) 2101-2106) report the cloning and expression in E. coli of a functional Fab fragment obtained from single human lymphocyte against anthrax toxin.

A method for preparing immunoglobulin libraries is reported in WO 2007/031550.

In WO 2011/147903 a single B-cell cultivation method, wherein the co-cultivating is in the presence of a synthetic feeder mix that comprises IL-1β, TNFα, IL-10, and one or more selected from IL-21, SAC, BAFF, IL-2, IL-4, and IL-6, is reported.

In WO 2013/076139 CD40L expressing mammalian cells and their use are reported.

In WO 2013/092716 a rapid method for cloning and expression of cognate antibody variable region gene segments is reported.

In U.S. Pat. No. 7,807,415 methods for producing stable immortalized B-lymphocytes are reported. In EP 0 488 470 methods for the production of antibodies are reported.

In WO 2015/000624 to co-cultivation of ovine B-cells and phorbol myristate acetate (PMA) is reported.

In US 2013/177987 methods for developing antigen-specific antibody-producing cell lines and monoclonal antibodies are reported.

A synthetic feeder mix consisting of IL-1β (interleukin-1 beta), TNF-α (tumor necrosis factor alpha), IL-2 (interleukin-2) and IL-10 (interleukin-10) is known from Tucci, A., et al., J. Immunol. 148 (1992) 2778-2784.

Other synthetic cytokine mixes are reported by Bovia, F. et al. (Blood 101 (2003) 1727-1733) and Werner-Favre (Eur. J. Immunol. 31 (2001) 243-249).

SUMMARY OF THE INVENTION

Herein is reported a method for the co-cultivation of single deposited B-cells, which can be of any source, with feeder cells in a suitable co-cultivation medium, wherein all cell growth stimulating additives are defined, e.g. of synthetic origin. In one embodiment neither of a thymocyte cultivation supernatant, a macrophage cultivation supernatant, or a T-cell cultivation supernatant is added to the cultivation.

The invention is based at least in part on the finding that phorbol myristate acetate alone or a combination of phorbol myristate acetate (PMA) with defined (synthetic) cytokines and defined (synthetic) interleukins can replace the commonly employed, non-defined macrophage/T-cell cultivation supernatant used in the co-cultivation of B-cells and feeder cells, such as murine EL4-B5 feeder cells.

The invention is further based at least in part on the finding that when employing phorbol myristate acetate in combination with defined (synthetic) cytokines and defined (synthetic) interleukins the concentrations of each of these components has to be within certain ranges in order to ensure a positive effect.

The individual aspects as reported herein are methods for i) the isolation of a B-cell or a B-cell clone from a population of B-cells, whereby the isolated B-cell or B-cell clone produces an antibody specifically binding to a target (antigen), ii) the co-cultivation of single deposited B-cells, and iii) the production of an antibody.

Concomitantly with the methods also the corresponding uses are also encompassed and disclosed.

One aspect as reported herein is a method for co-cultivating one or more B-cells (for the production of immunoglobulin) comprising the step of co-cultivating the one or more B-cells with feeder cells in the presence of phorbol myristate acetate (PMA) (and thereby producing immunoglobulin).

In one embodiment the co-cultivating is in the presence of 1.5-7.25 ng/ml phorbol myristate acetate.

In one embodiment the co-cultivating is in the absence of a cultivation supernatant of thymocytes (TSN). In one embodiment the method is without the addition of the cultivation supernatant of thymocytes (TSN).

In one embodiment the co-cultivating is further in the presence of *Staphylococcus aureus* strain Cowans cells (SAC).

One aspect as reported herein is a method for co-cultivating one or more B-cells (for the production of immunoglobulin) comprising the step of co-cultivating the one or more B-cells with feeder cells in the presence of phorbol myristate acetate (PMA), IL-1beta, TNFalpha, IL-2, IL-10 and IL-6 (and thereby producing immunoglobulin).

All embodiments are embodiments of all aspects as reported herein.

In one embodiment the amount of phorbol myristate acetate (PMA), IL-1beta, TNFalpha, IL-2, IL-10 and IL-6 used in the co-cultivation is given by weight.

In one embodiment the co-cultivating is in the presence of
about 0.3-3 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.

In one embodiment the co-cultivating is in the presence of
about 0.3-3 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.

In one embodiment the co-cultivating is in the presence of
about 0.9-3 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.

In one embodiment the co-cultivating is in the presence of
about 0.9-3 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.

In one embodiment the co-cultivating is in the presence of
about 0.9-3 ng/ml phorbol myristate acetate,
about 0.02 ng/ml (murine) IL-1beta,
about 0.02 ng/ml (murine) TNFalpha,
about 0.5 ng/ml (murine) IL-2,
about 0.1 ng/ml (murine) IL-10, and
about 0.1 ng/ml (murine) IL-6.

In one embodiment the co-cultivating is in the presence of
about 0.5-2.5 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.

In one embodiment the co-cultivating is in the presence of
about 0.5-2.5 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.

In one embodiment the co-cultivating is in the presence of
about 0.2-0.35 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.

In one embodiment the co-cultivating is in the presence of
about 0.2-0.35 ng/ml phorbol myristate acetate,
about 0.064 ng/ml (murine) IL-1beta,
about 0.064 ng/ml (murine) TNFalpha
about 1.6 ng/ml (murine) IL-2,
about 0.32 ng/ml (murine) IL-10, and
about 0.32 ng/ml (murine) IL-6.

In one embodiment the co-cultivating is in the presence of
about 0.05-0.7 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.

In one embodiment the co-cultivating is in the presence of
about 0.05-0.7 ng/ml phorbol myristate acetate,
about 0.2 ng/ml (murine) IL-1beta,
about 0.2 ng/ml (murine) TNFalpha,
about 5 ng/ml (murine) IL-2,
about 1 ng/ml (murine) IL-10, and
about 1 ng/ml (murine) IL-6.

In one embodiment the co-cultivating is in the presence of
about 0.05-0.7 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.

In one preferred embodiment the co-cultivating is in the presence of
about 1.3 ng/ml phorbol myristate acetate,
about 0.064 ng/ml (murine) IL-1beta
about 0.064 ng/ml (murine) TNFalpha,
about 1.6 ng/ml (murine) IL-2,
about 0.32 ng/ml (murine) IL-10, and
about 0.32 ng/ml (murine) IL-6.

In one preferred embodiment the co-cultivating is in the presence of
about 0.9 ng/ml phorbol myristate acetate,
about 0.02 ng/ml (murine) IL-1beta,
about 0.02 ng/ml (murine) TNFalpha,
about 0.5 ng/ml (murine) IL-2,
about 0.1 ng/ml (murine) IL-10, and
about 0.1 ng/ml (murine) IL-6.

In one embodiment the amount of phorbol myristate acetate (PMA) used in the co-cultivation is given by weight and the amount of IL-1beta, TNFalpha, IL-2, IL-10 and IL-6 used in the co-cultivation is given by (specific) activity.

In one embodiment the co-cultivating is in the presence of
about 0.3-3 ng/ml phorbol myristate acetate,
about 0.02-0.2 ng/ml with $5.5\text{-}14*10^8$ IU/mg (murine) IL-1beta,
about 0.02-0.2 ng/ml with $2.3\text{-}2.9*10^8$ U/mg (murine) TNFalpha, about 0.5-5 ng/ml with 6-7 (preferably 6.3)*$10^6$ IU/mg (murine) IL-2, about 0.1-1 ng/ml with 6-7.5*$10^5$ IU/mg (murine) IL-10, and about 0.1-1 ng/ml with 9.2-16.1*$10^8$ U/mg (murine) IL-6.

In one embodiment the co-cultivating is in the presence of about 0.3-3 ng/ml phorbol myristate acetate, about 0.064 ng/ml with 5.5-14*$10^8$ IU/mg (murine) IL-1beta, about 0.064 ng/ml with 2.3-2.9*$10^8$ U/mg (murine) TNFalpha, about 1.6 ng/ml with 6-7 (preferably 6.3)*$10^6$ IU/mg (murine) IL-2, about 0.32 ng/ml with 6-7.5*$10^5$ IU/mg (murine) IL-10, and about 0.32 ng/ml with 9.2-16.1*$10^8$ U/mg (murine) IL-6.

In one embodiment the co-cultivating is in the presence of about 0.9-3 ng/ml phorbol myristate acetate, about 0.02-0.2 ng/ml with 5.5-14*$10^8$ IU/mg (murine) IL-1beta, about 0.02-0.2 ng/ml with 2.3-2.9*$10^8$ U/mg (murine) TNFalpha, about 0.5-5 ng/ml with 6-7 (preferably 6.3)*$10^6$ IU/mg (murine) IL-2, about 0.1-1 ng/ml with 6-7.5*$10^5$ IU/mg (murine) IL-10, and about 0.1-1 ng/ml with 9.2-16.1*$10^8$ U/mg (murine) IL-6.

In one embodiment the co-cultivating is in the presence of about 0.9-3 ng/ml phorbol myristate acetate, about 0.064 ng/ml with 5.5-14*$10^8$ IU/mg (murine) IL-1beta, about 0.064 ng/ml with 2.3-2.9*$10^8$ U/mg (murine) TNFalpha, about 1.6 ng/ml with 6-7 (preferably 6.3)*$10^6$ IU/mg (murine) IL-2, about 0.32 ng/ml with 6-7.5*$10^5$ IU/mg (murine) IL-10, and about 0.32 ng/ml with 9.2-16.1*$10^8$ U/mg (murine) IL-6.

In one embodiment the co-cultivating is in the presence of about 0.9-3 ng/ml phorbol myristate acetate, about 0.02 ng/ml with 5.5-14*$10^8$ IU/mg (murine) IL-1beta, about 0.02 ng/ml with 2.3-2.9*$10^8$ U/mg (murine) TNFalpha, about 0.5 ng/ml with 6-7 (preferably 6.3)*$10^6$ IU/mg (murine) IL-2, about 0.1 ng/ml with 6-7.5*$10^5$ IU/mg (murine) IL-10, and about 0.1 ng/ml with 9.2-16.1*$10^8$ U/mg (murine) IL-6.

In one embodiment the co-cultivating is in the presence of about 0.5-2.5 ng/ml phorbol myristate acetate, about 0.02-0.2 ng/ml with 5.5-14*$10^8$ IU/mg (murine) IL-1beta, about 0.02-0.2 ng-ml with 2.3-2.9*$10^8$ U/mg (murine) TNFalpha, about 0.5-5 ng/ml with 6-7 (preferably 6.3)*$10^6$ IU/mg (murine) IL-2, about 0.1-1 ng/ml with 6-7.5*$10^5$ IU/mg (murine) IL-10, and about 0.1-1 ng/ml with 9.2-16.1*$10^8$ U/mg (murine) IL-6.

In one embodiment the co-cultivating is in the presence of about 0.5-2.5 ng/ml phorbol myristate acetate, about 0.064 ng/ml with 5.5-14*$10^8$ IU/mg (murine) IL-1beta, about 0.064 ng/ml with 2.3-2.9*$10^8$ U/mg (murine) TNFalpha, about 1.6 ng/ml with 6-7 (preferably 6.3)*$10^6$ IU/mg (murine) IL-2, about 0.32 ng/ml with 6-7.5*$10^5$ IU/mg (murine) IL-10, and about 0.32 ng/ml with 9.2-16.1*$10^8$ U/mg (murine) IL-6.

In one embodiment the co-cultivating is in the presence of about 0.2-0.35 ng/ml phorbol myristate acetate, about 0.02-0.2 ng/ml with 5.5-14*$10^8$ IU/mg (murine) IL-1beta, about 0.02-0.2 ng/ml with 2.3-2.9*$10^8$ U/mg (murine) TNFalpha, about 0.5-5 ng/ml with 6-7 (preferably 6.3)*$10^6$ IU/mg (murine) IL-2, about 0.1-1 ng/ml with 6-7.5*$10^5$ IU/mg (murine) IL-10, and about 0.1-1 ng/ml with 9.2-16.1*$10^8$ U/mg (murine) IL-6.

In one embodiment the co-cultivating is in the presence of about 0.2-0.35 ng/ml phorbol myristate acetate, about 0.064 ng/ml with 5.5-14*$10^8$ IU/mg (murine) IL-1beta, about 0.064 ng/ml with 2.3-2.9*$10^8$ U/mg (murine) TNFalpha, about 1.6 ng/ml with 6-7 (preferably 6.3)*$10^6$ IU/mg (murine) IL-2, about 0.32 ng/ml with 6-7.5*$10^5$ IU/mg (murine) IL-10, and about 0.32 ng/ml with 9.2-16.1*$10^8$ U/mg (murine) IL-6.

In one embodiment the co-cultivating is in the presence of about 0.05-0.7 ng/ml phorbol myristate acetate, about 0.02-0.2 ng/ml with 5.5-14*$10^8$ IU/mg (murine) IL-1beta, about 0.02-0.2 ng/ml with 2.3-2.9*$10^8$ U/mg (murine) TNFalpha, about 0.5-5 ng/ml with 6-7 (preferably 6.3)*$10^6$ IU/mg (murine) IL-2, about 0.1-1 ng/ml with 6-7.5*$10^5$ IU/mg (murine) IL-10, and about 0.1-1 ng/ml with 9.2-16.1*$10^8$ U/mg (murine) IL-6.

In one embodiment the co-cultivating is in the presence of about 0.05-0.7 ng/ml phorbol myristate acetate, about 0.2 ng/ml with 5.5-14*$10^8$ IU/mg (murine) IL-1beta, about 0.2 ng/ml with 2.3-2.9*$10^8$ U/mg (murine) TNFalpha, about 5 ng/ml with 6-7 (preferably 6.3)*$10^6$ IU/mg (murine) IL-2, about 1 ng/ml with 6-7.5*$10^5$ IU/mg (murine) IL-10, and about 1 ng/ml with 9.2-16.1*$10^8$ U/mg (murine) IL-6.

In one embodiment the co-cultivating is in the presence of about 0.05-0.7 ng/ml phorbol myristate acetate, about 0.064 ng/ml with 5.5-14*$10^8$ IU/mg (murine) IL-1beta, about 0.064 ng/ml with 2.3-2.9*$10^8$ U/mg (murine) TNFalpha, about 1.6 ng/ml with 6-7 (preferably 6.3)*$10^6$ IU/mg (murine) IL-2, about 0.32 ng/ml with 6-7.5*$10^5$ IU/mg (murine) IL-10, and about 0.32 ng/ml with 9.2-16.1*$10^8$ U/mg (murine) IL-6.

In one preferred embodiment the co-cultivating is in the presence of about 1.3 ng/ml phorbol myristate acetate, about 0.064 ng/ml with 5.5-14*$10^8$ IU/mg (murine) IL-1beta, about 0.064 ng/ml with 2.3-2.9*$10^8$ U/mg (murine) TNFalpha, about 1.6 ng/ml with 6-7 (preferably 6.3)*$10^6$ IU/mg (murine) IL-2, about 0.32 ng/ml with 6-7.5*$10^5$ IU/mg (murine) IL-10, and about 0.32 ng/ml with 9.2-16.1*$10^8$ U/mg (murine) IL-6.

In one preferred embodiment the co-cultivating is in the presence of about 0.9 ng/ml phorbol myristate acetate, about 0.02 ng/ml with 5.5-14*$10^8$ IU/mg (murine) IL-1beta, about 0.02 ng/ml with 2.3-2.9*$10^8$ U/mg (murine) TNFalpha, about 0.5 ng/ml with 6-7 (preferably 6.3)*$10^6$ IU/mg (murine) IL-2, about 0.1 ng/ml with 6-7.5*$10^6$ IU/mg (murine) IL-10, and about 0.1 ng/ml with 9.2-16.1*$10^8$ U/mg (murine) IL-6.

In one embodiment the co-cultivating is in the absence of a cultivation supernatant of thymocytes (TSN). In one embodiment the method is without the addition of the cultivation supernatant of thymocytes (TSN).

In one embodiment the feeder cells are (murine) EL4-B5 cells.

In one embodiment the co-cultivating is further in the presence of *Staphylococcus aureus* strain Cowans cells (SAC).

In one embodiment the method is for the co-cultivation of one B-cell. In one preferred embodiment the one B-cell is a single deposited B-cell.

In one embodiment the incubating is for 5 to 14 days.

One aspect as reported herein is a method for producing an antibody comprising the co-cultivation method as reported herein.

The result of the co-cultivation is a B-cell clone, i.e. a population of B-cells that are the progeny of a single B-cell.

In one embodiment the methods as reported herein comprise prior to the co-cultivating step the following step:

depositing those B-cells of a population of B-cells that have been labeled with (one to three) fluorescence dyes/fluorophores as single cells.

In one embodiment the methods as reported herein comprise prior to the co-cultivating step the following step:

depositing those B-cells of a population of B-cells as single cells that have been contacted with (two to four) antibodies each specifically binding to a different B-cell surface antigen, whereby each antibody is conjugated to a different fluorescent dye, (but labeled only with one to three fluorescence dyes).

The labeling is in one embodiment by contacting the B-cell population (sequentially or simultaneously) with (two to four) fluorescently labeled antibodies. Thereby a labeled B-cell preparation is obtained. Each of the fluorescently labeled antibodies binds to a different B-cell surface marker/target.

The depositing is by introducing the labeled B-cell preparation into a flow cytometer and depositing those cells as single cells that have been labeled with (one to three) fluorescent labels. As it is possible to incubate the cells with more fluorescent dyes as those which are used for selecting the cells in the cell sorter the cells can be selected for the presence of specific surface markers and (optionally) simultaneously for the absence of other surface markers.

The labeling and single cell deposition is done in order to reduce the complexity of the B-cell population by depleting those B-cells that are not likely to produce an antibody having the intended characteristics. The labeled antibodies bind to a specific polypeptide displayed on the surface of B-cells and, thus, provide for a positive selection label. Likewise, it is also possible to select cells that are only labeled with a reduced number of fluorescent dyes compared to the number of labeled antibodies with which the B-cell had been incubated, such as e.g. cells having one fluorescent label out of two (i.e. incubation with two fluorescently label antibodies has been performed but only one thereof binds to the B-cells). Based on the binding/non-binding of the fluorescently labeled antibodies to the individual B-cells of the B-cell population it is possible to identify and separate target B-cells using a microfluidic sorting apparatus. Concomitantly with the selection also the amount of the label can be determined.

In one embodiment the methods as reported herein comprise the step of incubating the population of B-cells in the co-cultivation medium prior to the single cell depositing/deposition. In one embodiment the incubating is at about 37° C. In one embodiment the incubating is for 0.5 to two hours. In one embodiment the incubating is for about one hour. In one preferred embodiment the incubating is at about 37° C. for about one hour.

In one embodiment the methods as reported herein comprise after the depositing step and before the co-cultivating step the step of centrifuging the single cell deposited B-cells. In one embodiment the centrifuging is for about 1 min. to about 30 min. In one embodiment the centrifuging is for about 5 min. In one embodiment the centrifuging is at about 100×g to about 1,000×g. In one embodiment the centrifuging is at about 300×g. In one preferred embodiment the centrifuging is for about 5 min. at about 300×g.

In one embodiment the method for selecting/obtaining a B-cell (clone) comprises the following steps:

a) labeling the B-cells of a population of B-cells with (one to three) fluorescent dyes (optionally by incubating the B-cell population with two to four fluorescently labeled antibodies specifically binding to two to four different pre-determined B-cell surface markers), b) optionally incubating the cells in co-cultivation medium, c) depositing those B-cells of the population of B-cells that have been labeled (with one to three fluorescent dyes) (and optionally not labeled with the other fluorescent dye(s)) as single cells, d) optionally centrifuging the single deposited B-cells.

e) (individually) co-cultivating each single deposited B-cell with feeder cells in a co-cultivation medium, which has been supplemented with a feeder mix, f) selecting a B-cell clone proliferating and secreting an antibody in step e).

In one embodiment the method for producing an antibody specifically binding to a target comprises the following steps a) labeling the B-cells of a population of B-cells with (one to three) fluorescent dyes (optionally by incubating the B-cell population with two to four fluorescently labeled antibodies specifically binding to two to four different pre-determined B-cell surface markers), b) optionally incubating the cells in co-cultivation medium, c) depositing those B-cells of the population of B-cells that have been labeled (with one to three fluorescent dyes) (and optionally not labeled with the other fluorescent dye(s)) as single cells, d) optionally centrifuging the single deposited B-cells, e) (individually) co-cultivating each single deposited B-cell with feeder cells in a co-cultivation medium, which has been supplemented with a feeder mix, f) selecting a B-cell clone of step e) secreting an antibody, g) i) obtaining one or more nucleic acids encoding the secreted antibody's variable domains from the B-cell clone selected in step f), ii) if the B-cell clone is not a human B-cell clone humanizing the variable domains and providing the respective encoding nucleic acids, and iii) introducing the one or more nucleic acids in one or more expression vectors, h) cultivating a cell, which has been transfected with the one or more expression vectors of step g), and recovering the antibody from the cell or the cultivation supernatant and thereby producing the antibody.

In one embodiment the method for producing an antibody comprising the following steps a) labeling the B-cells of a population of B-cells with (one to three) fluorescent dyes (optionally by incubating the B-cell population with two to four fluorescently labeled antibodies specifically binding to two to four different pre-determined B-cell surface markers), b) optionally incubating the cells in co-cultivation medium, c) depositing those B-cells of a population of B-cells that have been labeled (with one to three fluorescent dyes) (and optionally not labeled with the other fluorescent dye(s)) as single cells, d) optionally centrifuging the single deposited B-cells, e) (individually) co-cultivating each single deposited B-cell with feeder cells in a co-cultivation medium, which has been supplemented with a feeder mix, f) determining the binding specificity of the antibodies secreted in the cultivation medium of the individual B-cells, g) obtaining one or more nucleic acids encoding the secreted antibody's variable domains from the B-cell clone by a reverse transcriptase PCR and nucleotide sequencing, (and thereby obtaining a monoclonal antibody variable light and heavy chain domain encoding nucleic acid)

h) if the B-cell is a non-human B-cell humanizing the variable light and heavy chain domain and providing a nucleic acid encoding the humanized variable domains, i) introducing the monoclonal antibody variable light and heavy chain variable domain encoding nucleic acid in one or more expression vectors for the expression of an (human or humanized) antibody, j) introducing the expression vector(s) in a cell, k) cultivating the cell and recovering the antibody from the cell or the cell culture supernatant and thereby producing the antibody.

In one embodiment the obtaining one or more nucleic acids encoding the secreted antibody's variable domains from the B-cell clone comprises the following steps:

extracting total RNA from the antibody-producing B-cell clone, performing a single stranded cDNA synthesis/reverse transcription of the extracted polyA$^+$ mRNA, performing a PCR with a set of species specific primer, optionally removal of the PCR primer/purification of the PCR product, optionally sequencing of the PCR product.

In one embodiment the introducing the monoclonal antibody variable light and/or heavy chain variable domain encoding nucleic acid in an expression vector for the expression of an (human or humanized) antibody comprises the following steps:

T4 polymerase incubation of the variable light and heavy chain variable domain, linearization and amplification of the expression vector, T4 polymerase incubation of the amplified expression vector, sequence and ligation independent cloning of the variable domain encoding nucleic acid into the amplified expression vector, and preparation of the vector(s) from pool of vector transformed *E. coli* cells.

In one embodiment of all aspects the method comprises immediately prior to the labeling step the following step:

incubating the population of B-cells with (target) antigen, which is immobilized on a solid surface, and recovering (only) B-cells bound to the immobilized antigen.

In one embodiment of all aspects the population of B-cells is a non-human animal B-cell population. In one embodiment the B-cell population is a mouse B-cell population, or a hamster B-cell population, or a rabbit B-cell population. In one preferred embodiment the B-cell population is a rabbit B-cell population.

In one embodiment of all aspects the population of B-cells is obtained from the blood of a non-human animal 4 days after the immunization. In one embodiment the population of B-cells is obtained from the blood of a non-human animal of from 4 days up to at most 9 days after immunization.

In one embodiment the B-cell population is a human B-cell population.

In one embodiment of all aspects the population of B-cells is obtained from blood by density gradient centrifugation.

In one embodiment of all aspects the B-cells are mature B-cells.

In one embodiment of all aspects the single cells are deposited (individually) into the wells of a multi-well plate.

In one embodiment of all aspects the antibody is a monoclonal antibody.

In one embodiment of all aspects the deposited cells are labeled with one or three fluorescence dyes and the incubation is with two to four fluorescently labeled antibodies.

In one embodiment of all aspects the labeling of the B-cells of the population of B-cells results in labeling of 0.1% to 2.5% of the cells of the (total) B-cell population.

In one embodiment of all aspects the labeling is of B-cell surface IgG.

In one embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG$^+$IgM$^-$-B-cells).

In one embodiment of all aspects the incubation is with a fluorescently labeled anti-IgG antibody and a fluorescently labeled anti-light chain antibody (the labeling is of cell surface IgG and cell surface antibody light chain) and the selection is of cells positive for cell surface IgG and positive for cell surface antibody light chain (results in single cell deposition of IgG$^+$LC$^+$-B-cells).

In one embodiment of all aspects the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG$^+$IgM$^-$-B-cells), whereby the population of B-cells has been incubated with (target) antigen, which is immobilized on a solid surface, and (only) B-cells bound to the immobilized antigen have been recovered and subjected to the incubation with the fluorescently labeled antibodies.

In one embodiment of all aspects the incubation is with a fluorescently labeled anti-IgG antibody and a fluorescently labeled anti-CD19 antibody (the labeling is of cell surface IgG and cell surface CD19) and the selection is of cells positive for cell surface IgG and also positive for cell surface CD19 (results in single cell deposition of IgG⁺CD19⁺-B-cells).

In one embodiment of all aspects the incubation is with a fluorescently labeled anti-IgG antibody and a fluorescently labeled anti-CD38 antibody (the labeling is of cell surface IgG and cell surface CD38) and the selection is of cells positive for cell surface IgG and also positive for cell surface CD38 (results in single cell deposition of IgG⁺CD38⁺-B-cells).

In one embodiment of all aspects the incubation is with a fluorescently labeled anti-IgG antibody and a fluorescently labeled anti-CD138 antibody (the labeling is of cell surface IgG and cell surface CD138) and the selection is of cells negative for cell surface IgG and positive for cell surface CD138 (results in single cell deposition of IgG⁻CD138⁺-B-cells).

In one embodiment of all aspects the incubation is with a fluorescently labeled anti-IgG antibody and a fluorescently labeled anti-CD268 antibody (the labeling is of cell surface IgG and cell surface CD268) and the selection is of cells positive for cell surface IgG and also positive for cell surface CD269 (results in single cell deposition of IgG⁺CD268⁺-B-cells).

In one embodiment of all aspects the incubation is with a fluorescently labeled anti-CD27 antibody and a fluorescently labeled anti-CD138 antibody (the labeling is of cell surface CD27 and cell surface CD138) and the selection is of cells positive for cell surface CD27 and also positive for cell surface CD138 (results in single cell deposition of CD27⁺CD138⁺-B-cells).

In one embodiment of all aspects the incubation is with a fluorescently labeled anti-CD3 antibody and a fluorescently labeled anti-CD27 antibody (the labeling is of cell surface CD3 and cell surface CD27) and the selection is of cells negative for cell surface CD3 and also positive for cell surface CD27 (results in single cell deposition of CD3⁻CD19⁺-B-cells).

In one embodiment of all previous embodiment the incubation is in addition with a fluorescently labeled anti-light chain antibody (the labeling is of cell surface antibody light chain in addition to the other two labels) and the selection is of cells positive for cell surface antibody light chain (results in single cell deposition of LC-B-cells).

In one embodiment of all aspects the B-cell population is a rabbit B-cell population and the incubation is with a fluorescently labeled anti-IgG antibody (the labeling is of cell surface IgG) and the selection is of cells positive for cell surface IgG (results in single cell deposition of IgG⁺-B-cells).

In one embodiment of all aspects the B-cell population is a rabbit B-cell population and the incubation is with a fluorescently labeled anti-CD138 antibody (the labeling is of cell surface CD138) and the selection is of cells positive for cell surface CD138 (results in single cell deposition of CD138⁺-B-cells).

In one embodiment of all aspects the B-cell population is a rabbit B-cell population and the incubation is with a fluorescently labeled anti-IgG antibody and a fluorescently labeled anti-CD138 antibody (the labeling is of cell surface IgG and cell surface CD138) and the selection is of cells positive for cell surface IgG and also positive for cell surface CD138 (results in single cell deposition of IgG⁺CD138⁺-B-cells).

In one preferred embodiment of all aspects the B-cell population is a rabbit B-cell population and the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG⁺IgM⁻-B-cells).

In one embodiment of all previous embodiment the incubation of the rabbit B-cells is in addition with a fluorescently labeled anti-light chain antibody (the labeling is of cell surface antibody light chain in addition to the other two labels) and the selection is of cells positive for cell surface antibody light chain (results in single cell deposition of LC⁺-B-cells).

In one embodiment of all aspects the B-cell population is a hamster B-cell population and the incubation is with a fluorescently labeled anti-IgG antibody and a fluorescently labeled anti-IgM antibody (the labeling is of cell surface IgG and cell surface IgM) and the selection is of cells positive for cell surface IgG and negative for cell surface IgM (results in single cell deposition of IgG⁺IgM⁻-B-cells).

In one embodiment of all aspects the B-cell population is a murine B-cell population and the incubation is with a fluorescently labeled anti-IgG antibody (the labeling is of cell surface IgG) and the selection is of cells positive for cell surface IgG (results in single cell deposition of IgG⁺-B-cells).

In one embodiment of all aspects the B-cell population is a murine B-cell population and the incubation is with a fluorescently labeled anti-IgG antibody and a fluorescently labeled anti-CD19 antibody (the labeling is of cell surface IgG and cell surface CD19) and the selection is of cells positive for cell surface IgG and also positive for cell surface CD19 (results in single cell deposition of IgG⁺CD19⁺-B-cells).

In one embodiment of all aspects the B-cell population is a murine B-cell population and the incubation is with a fluorescently labeled anti-IgG antibody and a fluorescently labeled anti-CD138 antibody (the labeling is of cell surface IgG and cell surface CD138) and the selection is of cells negative for cell surface IgG and positive for cell surface CD138 (results in single cell deposition of IgG⁻CD138⁺-B-cells).

In one embodiment of all aspects the co-cultivating is in a co-cultivation medium comprising RPMI 1640 medium supplemented with 10% (v/v) FCS, 1% (w/v) of a 200 mM glutamine solution that comprises penicillin and streptomycin, 2% (v/v) of a 100 mM sodium pyruvate solution, and 1% (v/v) of a 1 M 2-(4-(2-hydroxyethyl)-1-piperazine)-ethane sulfonic acid (HEPES) buffer. In one embodiment the co-cultivation medium further comprises 0.05 mM beta-mercaptoethanol.

In one embodiment the animal is an experimental animal. In one embodiment the experimental animal is selected from mouse, hamster, and rabbit. In one embodiment the experimental animal is a rabbit.

One aspect as reported herein is a (defined and/or synthetic) feeder mix comprising phorbol myristate acetate (PMA), IL-1beta, TNFalpha, IL-2, IL-10 and IL-6.

In one embodiment the (synthetic) feeder mix comprises
    about 0.3-3 ng/ml phorbol myristate acetate,
    about 0.02-0.2 ng/ml (murine) IL-1beta,
    about 0.02-0.2 ng/ml (murine) TNFalpha,

about 0.5-5 ng/ml (murine) IL-2,
about 0.1-1 ng/ml (murine) IL-10, and
about 0.1-1 ng/ml (murine) IL-6.
In one embodiment the (synthetic) feeder mix comprises
about 0.3-3 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.
In one embodiment the (synthetic) feeder mix comprises
about 0.9-3 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.
In one embodiment the (synthetic) feeder mix comprises
about 0.9-3 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.
In one embodiment the (synthetic) feeder mix comprises
about 0.9-3 ng/ml phorbol myristate acetate,
about 0.02 ng/ml (murine) IL-1beta,
about 0.02 ng/ml (murine) TNFalpha,
about 0.5 ng/ml (murine) IL-2,
about 0.1 ng/ml (murine) IL-10, and
about 0.1 ng/ml (murine) IL-6.
In one embodiment the (synthetic) feeder mix comprises
about 0.5-2.5 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.
In one embodiment the (synthetic) feeder mix comprises
about 0.5-2.5 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.
In one embodiment the (synthetic) feeder mix comprises
about 0.2-0.35 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.
In one embodiment the (synthetic) feeder mix comprises
about 0.2-0.35 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.
In one embodiment the (synthetic) feeder mix comprises
about 0.05-0.7 ng/ml phorbol myristate acetate,
about 0.02-0.2 ng/ml (murine) IL-1beta,
about 0.02-0.2 ng/ml (murine) TNFalpha,
about 0.5-5 ng/ml (murine) IL-2,
about 0.1-1 ng/ml (murine) IL-10, and
about 0.1-1 ng/ml (murine) IL-6.

In one embodiment the (synthetic) feeder mix comprises
about 0.05-0.7 ng/ml phorbol myristate acetate,
about 0.2 ng/ml (murine) IL-1beta,
about 0.2 ng/ml (murine) TNFalpha,
about 5 ng/ml (murine) IL-2,
about 1 ng/ml (murine) IL-10, and
about 1 ng/ml (murine) IL-6.
In one embodiment the (synthetic) feeder mix comprises
about 0.05-0.7 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.
In one preferred embodiment the (synthetic) feeder mix comprises
about 1.3 ng/ml phorbol myristate acetate,
about 0.064 ng/ml (murine) IL-1beta,
about 0.064 ng/ml (murine) TNFalpha,
about 1.6 ng/ml (murine) IL-2,
about 0.32 ng/ml (murine) IL-10, and
about 0.32 ng/ml (murine) IL-6.
In one preferred embodiment the (synthetic) feeder mix comprises
about 0.9 ng/ml phorbol myristate acetate,
about 0.02 ng/ml (murine) IL-1beta,
about 0.02 ng/ml (murine) TNFalpha,
about 0.5 ng/ml (murine) IL-2,
about 0.1 ng/ml (murine) IL-10, and
about 0.1 ng/ml (murine) IL-6.
In one embodiment the (synthetic) feeder mix comprises
about 0.3-3 ng/ml phorbol myristate acetate,
about 0.02-0.2 ng/ml with $5.5\text{-}10*10^8$ IU/mg (murine) IL-1beta,
about 0.02-0.2 ng/ml with $2.3\text{-}2.9*10^8$ U/mg (murine) TNFalpha,
about 0.5-5 ng/ml with 6-7 (preferably $6.3)*10^6$ IU/mg (murine) IL-2,
about 0.1-1 ng/ml with $6\text{-}7.5*10^5$ IU/mg (murine) IL-10, and
about 0.1-1 ng/ml with $9.2\text{-}16.1*10^8$ U/mg (murine) IL-6.
In one embodiment the (synthetic) feeder mix comprises
about 0.3-3 ng/ml phorbol myristate acetate,
about 0.064 ng/ml with $5.5\text{-}14*10^8$ IU/mg (murine) IL-1beta,
about 0.064 ng/ml with $2.3\text{-}2.9*10^8$ U/mg (murine) TNFalpha,
about 1.6 ng/ml with 6-7 (preferably $6.3)*10^6$ IU/mg (murine) IL-2,
about 0.32 ng/ml with $6\text{-}7.5*10^5$ IU/mg (murine) IL-10, and
about 0.32 ng/ml with $9.2\text{-}16.1*10^8$ U/mg (murine) IL-6.
In one embodiment the (synthetic) feeder mix comprises
about 0.9-3 ng/ml phorbol myristate acetate,
about 0.02-0.2 ng/ml with $5.5\text{-}14*10^8$ IU/mg (murine) IL-1beta,
about 0.02-0.2 ng/ml with $2.3\text{-}2.9*10^8$ U/mg (murine) TNFalpha,
about 0.5-5 ng/ml with 6-7 (preferably $6.3)*10^6$ IU/mg (murine) IL-2,
about 0.1-1 ng/ml with $6\text{-}7.5*10^5$ IU/mg (murine) IL-10, and
about 0.1-1 ng/ml with $9.2\text{-}16.1*10^8$ U/mg (murine) IL-6.
In one embodiment the (synthetic) feeder mix comprises
about 0.9-3 ng/ml phorbol myristate acetate,
about 0.064 ng/ml with $5.5\text{-}14*10^8$ IU/mg (murine) IL-1beta, about 0.064 ng/ml with 2.3-2.9*10$^8$ U/mg (murine) TNFalpha, about 1.6 ng/ml with 6-7 (preferably 6.3)*10$^6$ IU/mg (murine) IL-2, about 0.32 ng/ml with 6-7.5*10$^5$ IU/mg (murine) IL-10, and about 0.32 ng/ml with 9.2-16.1*10$^8$ U/mg (murine) IL-6.

In one embodiment the (synthetic) feeder mix comprises about 0.9-3 ng/ml phorbol myristate acetate, about 0.02 ng/ml with 5.5-14*10$^8$ IU/mg (murine) IL-1beta, about 0.02 ng/ml with 2.3-2.9*10$^8$ U/mg (murine) TNFalpha, about 0.5 ng/ml with 6-7 (preferably 6.3)*10$^6$ IU/mg (murine) IL-2, about 0.1 ng/ml with 6-7.5*10$^5$ IU/mg (murine) IL-10, and about 0.1 ng/ml with 9.2-16.1*10$^8$ U/mg (murine) IL-6.

In one embodiment the (synthetic) feeder mix comprises about 0.5-2.5 ng/ml phorbol myristate acetate, about 0.02-0.2 ng/ml with 5.5-14*10$^8$ IU/mg (murine) IL-1beta, about 0.02-0.2 ng/ml with 2.3-2.9*10$^8$ U/mg (murine) TNFalpha, about 0.5-5 ng/ml with 6-7 (preferably 6.3)*10$^6$ IU/mg (murine) IL-2, about 0.1-1 ng/ml with 6-7.5*10$^5$ IU/mg (murine) IL-10, and about 0.1-1 ng/ml with 9.2-16.1*10$^8$ U/mg (murine) IL-6.

In one embodiment the (synthetic) feeder mix comprises about 0.5-2.5 ng/ml phorbol myristate acetate, about 0.064 ng/ml with 5.5-14*10$^8$ IU/mg (murine) IL-1beta, about 0.064 ng/ml with 2.3-2.9*10$^8$ U/mg (murine) TNFalpha, about 1.6 ng/ml with 6-7 (preferably 6.3)*10$^6$ IU/mg (murine) IL-2, about 0.32 ng/ml with 6-7.5*10$^5$ IU/mg (murine) IL-10, and about 0.32 ng/ml with 9.2-16.1*10$^8$ U/mg (murine) IL-6.

In one embodiment the (synthetic) feeder mix comprises about 0.2-0.35 ng/ml phorbol myristate acetate, about 0.02-0.2 ng/ml with 5.5-14*10$^8$ IU/mg (murine) IL-1beta, about 0.02-0.2 ng/ml with 2.3-2.9*10$^8$ U/mg (murine) TNFalpha, about 0.5-5 ng/ml with 6-7 (preferably 6.3)*10$^6$ IU/mg (murine) IL-2, about 0.1-1 ng/ml with 6-7.5*10$^5$ IU/mg (murine) IL-10, and about 0.1-1 ng/ml with 9.2-16.1*10$^8$ U/mg (murine) IL-6.

In one embodiment the (synthetic) feeder mix comprises about 0.2-0.35 ng/ml phorbol myristate acetate, about 0.064 ng/ml with 5.5-14*10$^8$ IU/mg (murine) IL-1beta, about 0.064 ng/ml with 2.3-2.9*10$^8$ U/mg (murine) TNFalpha, about 1.6 ng/ml with 6-7 (preferably 6.3)*10$^6$ U/mg (murine) IL-2, about 0.32 ng/ml with 6-7.5*10$^5$ IU/mg (murine) IL-10, and about 0.32 ng/ml with 9.2-16.1*10$^8$ U/mg (murine) IL-6.

In one embodiment the (synthetic) feeder mix comprises about 0.05-0.7 ng/ml phorbol myristate acetate, about 0.02-0.2 ng/ml with 5.5-14*10$^8$ IU/mg (murine) IL-1beta, about 0.02-0.2 ng/ml with 2.3-2.9*10$^8$ U/mg (murine) TNFalpha, about 0.5-5 ng/ml with 6-7 (preferably 6.3)*10$^6$ IU/mg (murine) IL-2, about 0.1-1 ng/ml with 6-7.5*10$^5$ IU/mg (murine) IL-10, and about 0.1-1 ng/ml with 9.2-16.1*10$^8$ U/mg (murine) IL-6.

In one embodiment the (synthetic) feeder mix comprises about 0.05-0.7 ng/ml phorbol myristate acetate, about 0.2 ng/ml with 5.5-14*10$^8$ IU/mg (murine) IL-1beta, about 0.2 ng/ml with 2.3-2.9*10$^8$ U/mg (murine) TNFalpha, about 5 ng/ml with 6-7 (preferably 6.3)*10$^6$ IU/mg (murine) IL-2, about 1 ng/ml with 6-7.5*10$^5$ IU/mg (murine) IL-10, and about 1 ng/ml with 9.2-16.1*10$^8$ U/mg (murine) IL-6.

In one embodiment the (synthetic) feeder mix comprises about 0.05-0.7 ng/ml phorbol myristate acetate, about 0.064 ng/ml with 5.5-14*10$^8$ IU/mg (murine) IL-1beta, about 0.064 ng/ml with 2.3-2.9*10$^8$ U/mg (murine) TNFalpha, about 1.6 ng/ml with 6-7 (preferably 6.3)*10$^6$ IU/mg (murine) IL-2, about 0.32 ng/ml with 6-7.5*10$^5$ IU/mg (murine) IL-10, and about 0.32 ng/ml with 9.2-16.1*10$^8$ U/mg (murine) IL-6.

In one embodiment the (synthetic) feeder mix comprises about 1.3 ng/ml phorbol myristate acetate, about 0.064 ng/ml with 5.5-14*10$^8$ IU/mg (murine) IL-1beta, about 0.064 ng/ml with 2.3-2.9*10$^8$ U/mg (murine) TNFalpha, about 1.6 ng/ml with 6-7 (preferably 6.3)*10$^6$ IU/mg (murine) IL-2, about 0.32 ng/ml with 6-7.5*10$^5$ IU/mg (murine) IL-10, and about 0.32 ng/ml with 9.2-16.1*10$^8$ U/mg (murine) IL-6.

In one embodiment the (synthetic) feeder mix comprises about 0.9 ng/ml phorbol myristate acetate, about 0.02 ng/ml with 5.5-14*10$^8$ IU/mg (murine) IL-1beta, about 0.02 ng/ml with 2.3-2.9*10$^8$ U/mg (murine) TNFalpha, about 0.5 ng/ml with 6-7 (preferably 6.3)*10$^6$ IU/mg (murine) IL-2, about 0.1 ng/ml with 6-7.5*10$^5$ IU/mg (murine) IL-10, and about 0.1 ng/ml with 9.2-16.1*10$^8$ U/mg (murine) IL-6.

In one embodiment of all aspects the B-cell is a rabbit B-cell.

Definitions

The term "activity" denotes the biological effect of a compound in a specific assay.

In one embodiment the activity of TNFalpha is determined involving the cultivation of a sensitive cell line, such as ML929, with titrations of the test sample followed by observations for cytolysis by morphologic examination of stained cells or by measurement of the release of [3H] thymidine from pre-labeled cells (see e.g. Jensen, J. B., et al., Infect. Immun. 55 (1987) 1722-1724; Mannel, D. N., et al., Infect. Immun. 30 (1980) 523-530; Ruff, M. R. and G. E. Gifford, Infect. Immun. 31 (1981) 380-385).

In one embodiment the activity of IL-1beta is determined in a cell proliferation assay using D10.G4.1 mouse helper T cells; readout is D10.G4.1 proliferation (see, e.g., Symons, J. A., et al. (1987) in Lymphokines and Interferons, a Practical Approach. Clemens, M. J. et al. (Eds): IRL Press. page 272; Orencole, S. F. and Dinarello, C. A., Cytokine 1 (1989) 14-22).

In one embodiment the activity of IL-2 is determined as the proliferative effect of IL-2 on the murine cytotoxic T cell-line, CTLL-2; readout is proliferation (see, e.g., Weston, L., et al., Immunol. Cell Biol. 76 (1998) 190-192; Wadhwa, M., et al., J. Immunol. Meth. 397 (2013) 1-7).

In one embodiment the activity of IL-10 is determined in a co-stimulation bioassay with IL-4 (e.g. 5 pg/ml) using murine MC/9 cells; readout is proliferation (see, e.g., Imlach, W., et al., J. Gen. Virol. 83 (2002) 1049-1058; Thompson-Snipes, L., et al., J. Exp. Med. 173 (1991) 507-510).

In one embodiment the activity of IL-6 is determined using the murine 7TD1 cell line (hybridoma derived from cell fusion of LPS activated B lymphocytes and SP2/0-AG14 murine plasmacytoma cell line; Van Snick, J., et al., Proc. Natl. Acad. Sci. U.S.A., 83 (1986) 9679-9683), which are IL-6 growth and survival dependent; readout is proliferation (see, e.g., Manfredini, R., et al., Peptides 24 (2003) 1207-1220; Hausherr, A., et al., Oncogene 26 (2000) 4987-4998).

The term "antibody" herein is used to denote naturally occurring antibodies including their naturally occurring structural variants.

For example, native (human, mouse, rat, rabbit) IgG antibodies are heterotetrameric glycoproteins with a molecular weight of about 150,000 Dalton. Native IgG antibodies are composed of two identical light chains and two identical heavy chains comprising inter- and intra-chain disulfide bonds, so that all four chains are covalently linked to each other. From N- to C-terminus, each heavy chain has a variable region (VH), also called a variable heavy chain domain or a heavy chain variable domain, followed by three constant domains (CH1, CH2, and CH3), whereby a flexible hinge region is located between the first and the second constant domain. The heavy chain of an antibody may be assigned to one of five types, called IgA, IgD, IgE, IgG and IgM, depending on their sequence and domain structure ("class" of an antibody). Several of these may be further divided into subclasses (isotypes), e.g., IgG1, IgG2, IgG3, IgG4, IgA1, and IgA2. The heavy chain constant domains that correspond to the different classes of immunoglobulins are called α, δ, ε, γ, and μ, respectively. Similarly, from N- to C-terminus, each light chain has a variable region (VL), also called a variable light chain domain or a light chain variable domain, followed by a constant light chain domain (CL). The light chain of an antibody may be assigned to one of two types, called kappa (κ) and lambda (λ), based on the amino acid sequence of its constant domain.

For example, native (camelid, i.e. from Camelidae, sub-order Tylopoda, which includes camels, dromedaries and llamas) heavy-chain only antibodies (VHH antibodies) do not comprise a classical CH1 domain as found in conventional IgG heavy chains, and, thus, are expressed as VHH domains fused directly to the hinge-CH2-CH3 domains of an antibody. The variable region sequences from llama derived VHH antibodies, for example, are similar to sequences in the human VH3 family of variable domains (Schroeder et al., Int. Immunol. 2 (1989) 41-50). Compared to antibodies of the IgG type the CDR3 domain amino acid sequence in L. llama VHH domains is longer on average than most CDR3 domains of classical IgG type antibodies comprising heavy and light chains. Alike classical IgG antibodies the position of the CDRs in VHH antibodies can be determined by methods well known in the art (see e.g. U.S. Pat. No. 5,637,677). Residues 11, 37, 44, 45 and 47 are important for the formation of the chain interface (see e.g. WO 99/42077).

An "antibody fragment" refers to a molecule other than an intact antibodies (IgG/VHH=four chain/two chain) comprising only a portion of an intact antibody and that binds to the same antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); single domain antibodies; and multispecific antibodies formed from antibody fragments.

The term "cell" includes both prokaryotic cells, which are used for propagation of plasmids, and eukaryotic cells, which are used for the expression of a nucleic acid. In one embodiment the eukaryotic cell is a mammalian cell. In one embodiment the mammalian cell is a CHO cell, optionally a CHO K1 cell (e.g. a ATCC CCL-61 or DSM ACC 110), or a CHO DG44 cell (also known as CHO-DHFR[−], e.g. a DSM ACC 126), or a CHO XL99 cell, a CHO-T cell (see e.g. Morgan, D., et al., Biochemistry 26 (1987) 2959-2963), or a CHO-S cell, or a Super-CHO cell (Pak, S. C. O., et al. Cytotechnol. 22 (1996) 139-146), or BHK cell, or aNS0 cell, or a Sp2/0 cell, or a HEK 293 cell, or a HEK 293 EBNA cell, or a PER.C6® cell, or a COS cell. If these cells are not adapted to growth in serum-free medium or in suspension an adaptation prior to the use in the current method can be performed. As used herein, the expression "cell" includes the subject cell and its progeny. Thus, the words "transformant" and "transformed cell" include the primary subject cell and cultures derived there from without regard for the number of transfers or sub-cultivations. It is also understood that all progeny may not be precisely identical in DNA content, due to deliberate or inadvertent mutations. Variant progeny that have the same function or biological activity as screened for in the originally transformed cell are included.

The term "clone" denotes a population of dividing and antibody secreting B-cells arising from/originating from a single B-cell. Thus, a B-cell clone is a homogeneous population of B-cells and produces a monoclonal antibody.

The term "experimental animal" denotes a non-human animal. In one embodiment the experimental animal is selected from rat, mouse, hamster, rabbit, camel, llama, non-human primates, sheep, dog, cow, chicken, amphibians, sharks and reptiles. In one embodiment the experimental animal is a rabbit.

The term "expression" as used herein refers to transcription and/or translation and secretion processes occurring within a cell. The level of transcription of a nucleic acid sequence of interest in a cell can be determined on the basis of the amount of corresponding mRNA that is present in the cell. For example, mRNA transcribed from a sequence of interest can be quantified by qPCR or RT-PCR or by Northern hybridization (see Sambrook, et al., Molecular Cloning: A Laboratory Manual, Second Edition, Cold Spring Harbor Laboratory Press, Cold Spring Harbor, N.Y. (1989)). Polypeptides encoded by a nucleic acid can be quantified by various methods, e.g. by ELISA, by assaying the biological activity of the polypeptide, or by employing assays that are independent of such activity, such as Western blotting or radioimmunoassay, using immunoglobulins that recognize and bind to the polypeptide (see Sambrook, et al., (1989), supra).

To a person skilled in the art procedures and methods are well known to convert an amino acid sequence, e.g. of a polypeptide, into a corresponding nucleic acid sequence encoding this amino acid sequence and vice versa. Therefore, a nucleic acid is characterized by its nucleic acid sequence consisting of individual nucleotides and likewise by the amino acid sequence of a polypeptide encoded thereby.

An "expression cassette" denotes a construct that contains the necessary regulatory elements, such as promoter and polyadenylation site, for expression of at least the contained nucleic acid in a cell.

Expression can be performed either as transient expression or a stable expression. Antibodies are in general secreted into the cultivation medium by the cell producing it. Therefore non-mature antibody chains contain an N-terminal extension (also known as the signal sequence), which is necessary for the transport/secretion of the antibody through the cell wall into the extracellular medium. In general, the signal sequence for recombinant production of an antibody can be derived from any gene encoding a secreted polypeptide. If a heterologous signal sequence is used, it should be one that is recognized and processed (i.e. cleaved by a signal peptidase) by the host cell. For secretion in yeast for example the native signal sequence of a heterologous gene to be expressed may be substituted by a homologous yeast signal sequence derived from a secreted gene, such as the yeast invertase signal sequence, alpha-factor leader (including *Saccharomyces, Kluyveromyces, Pichia*, and *Hansenula* α-factor leaders, the second described in U.S. Pat. No. 5,010,182), acid phosphatase signal sequence, or the *C. albicans* glucoamylase signal sequence (EP 0 362 179). In mammalian cells the native signal sequence is satisfactory, although other mammalian signal sequences may be suitable, such as signal sequences from other secreted polypeptides of the same or related species as well as viral secretory signal sequences, for example, the herpes simplex glycoprotein D signal sequence. The DNA fragment encoding for such a pre-segment is ligated in frame, i.e. operably linked, to the DNA fragment encoding an antibody chain.

The term "expression machinery" denotes the sum of the enzymes, cofactors, etc. of a cell that is involved in the steps of gene expression beginning with the transcription step of a nucleic acid or gene (i.e. also called "gene expression machinery") to the post-translational modification of the polypeptide encoded by the nucleic acid. The expression machinery e.g. comprises the steps of transcription of DNA into pre-mRNA, pre-mRNA splicing to mature mRNA, translation into a polypeptide of the mRNA, and post translational modification of the polypeptide.

An "expression plasmid" or "expression vector" is a nucleic acid providing all required elements for the expression of the comprised structural gene(s) in a host cell. Typically, an expression plasmid/vector comprises a prokaryotic plasmid propagation unit, e.g. for *E. coli*, comprising an origin of replication, and a selectable marker, a eukaryotic selection marker, and one or more expression cassettes for the expression of the structural gene(s) of interest each comprising a promoter, a structural gene, optionally a transcription terminator and a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "feeder mix" denotes a combination of different additives, such as growth factors, cytokines and/or further proteins promoting the activation and/or survival of B-cells and/or antibody secretion. The feeder mix is in no case herein a natural feeder mix, i.e. it is not obtained from the cultivation supernatant of thymocytes (TSN), which is a non-defined combination of cytokines. In the methods as reported herein the feeder mix is a synthetic feeder mix, which is a defined combination of different recombinantly produced or chemically synthesized additives, i.e. of growth factors, cytokines, interleukins and PMA, which promotes the activation and/or survival of B-cells and/or antibody secretion.

The terms "host cell", "host cell line", and "host cell culture" are used interchangeably and refer to cells into which exogenous nucleic acid has been introduced, including the progeny of such cells. Host cells include "transformants" or "transfectants" and "transformed cells" and "transfected cells", which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is an antibody, which possesses an amino acid sequence that corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

An "individual" or "subject" is a vertebrate. In one embodiment the vertebrate is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human. In other embodiments the individual or subject is a rabbit.

The term "labeling" denotes a process for determining the presence or absence of a surface marker, which can be determined by binding/non-binding of a specifically binding and labeled anti-surface marker antibody to a cell. Thus, the presence of a surface marker is determined e.g. in the case of a fluorescence label by the occurrence of a fluorescence whereas the absence of a surface marker is determined by the absence of a fluorescence after incubation of a cell or a population of cells with the respective specifically binding and labeled anti-surface marker antibody.

The term "monoclonal antibody" as used herein refers to an antibody obtained from a population of substantially homogeneous antibodies produced by a single cell clone, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to methods utilizing transgenic animals containing all or part of the human immunoglobulin loci, such methods and other exemplary methods for making monoclonal antibodies being described herein.

The term "PMA" denotes phorbol-12-myristate-13-acetate, a small chemical compound. The IUPAC name thereof is (1aR,1bS,4aR,7aS,7bS,8R,9R,9aS)-9a-(acetyloxy)-4a,7b-dihydroxy-3-(hydroxymethyl)-1,1,6,8-tetramethyl-5-oxo-1a,1b,4,4a,5,7a,7b,8,9,9a-decahydro-H-cyclopropa[3,4]benzo[1,2-e]azulen-9-yl myristate. This compound is also denoted as TPA, 12-O-tetradecanoylphorbol-13-acetate, tetradecanoylphorbol acetate, tetradecanoyl phorbol acetate, phorbol myristate acetate, 12-O-tetradecanoylphorbol 13-acetate, 12-tetradecanoylphorbol 13-acetate, 12-tetradecanoylphorbol 13-monoacetate, 13-O-acetylphorbol 12-myristate, 4β-phorbol 12-myristate 13-acetate, myristic acid, 9-ester with 1,1aα,1bβ,4,4a,7aα,7b,8,9,9a-decahydro-4aβ, 7bα,9β,9aα-tetrahydroxy-3-(hydroxymethyl)-1,1,6, 8α-tetramethyl-5H-cyclopropa[3,4]benz[1,2-e]azulen-5-one 9a-acetate, (+)-, phorbol 12-myristate 13-acetate, phorbol 12-tetradecanoate 13-acetate, phorbol myristate acetate, PMA, PMA (tumor promoter), tetradecanoic acid, (1aR,1bS,4aR,7aS,7bS,8R,9R,9aS)-9a-(acetyloxy)-1a,1b,4, 4a,5,7a,7b,8,9,9a-decahydro-4a,7bdihydroxy-3-(hydroxymethyl)-1,1,6,8-tetramethyl-5-oxo-1H-cyclopropa[3,4]benz [1,2-e]azulen-9-yl ester, tetradecanoic acid, 9a-(acetyloxy)-1a,1b,4,4a,5,7a,7b,8,9,9a-decahydro-4a,7b-dihydroxy-3-(hydroxymethyl)-1,1,6,8-tetramethyl-5-oxo-1H-cyclopropa [3,4]benz[1,2-e]azulen-9-yl ester, [1aR(1aα,1bβ,4aβ,7aα, 7bα,8α,9β,9aα)]-, TPA and TPA (phorbol derivative).

A "transfection plasmid/vector" is a nucleic acid (also denoted as nucleic acid molecule) providing all required elements for the expression of the in the transfection plasmid/vector comprised coding nucleic acids/structural gene(s) in a host cell. A transfection plasmid/vector comprises a prokaryotic plasmid propagation unit, e.g. for *E. coli*, in turn comprising a prokaryotic origin of replication, and a nucleic acid conferring resistance to a prokaryotic selection agent, further comprises the transfection plasmid/vector one or more nucleic acid(s) conferring resistance to an eukaryotic selection agent, and one or more nucleic acid encoding a polypeptide of interest. The nucleic acids conferring resistance to a selection agent and the nucleic acid(s) encoding a polypeptide of interest are placed each within an expression cassette, whereby each expression cassette comprises a promoter, a coding nucleic acid, and a transcription terminator including a polyadenylation signal. Gene expression is usually placed under the control of a promoter, and such a structural gene is said to be "operably linked to" the promoter. Similarly, a regulatory element and a core promoter are operably linked if the regulatory element modulates the activity of the core promoter.

The term "variable region" or "variable domain" refers to the region of an antibody heavy or light chain that is involved in the binding of the antibody to its antigen. The variable domains of the heavy chain and light chain (VH and VL, respectively) of a native antibody generally have similar structures, with each domain comprising four conserved framework regions (FRs) and three hypervariable regions (HVRs) (see, e.g., Kindt, T. J., et al., Kuby Immunology, 6th ed., W.H. Freeman and Co., N.Y. (2007), page 91). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "young animal" denotes an animal before sexual maturity occurs. A young hamster, for example, is of an age of less than 6 weeks, especially less than 4 weeks. A young mouse, for example, is of an age of less than 8 weeks, especially less than 5 weeks.

DETAILED DESCRIPTION OF THE INVENTION

The invention is based at least in part on the finding that phorbol myristate acetate alone or a combination of phorbol myristate acetate (PMA) with synthetic cytokines and synthetic interleukins can replace the commonly employed macrophage/T-cell cultivation supernatant used in the co-cultivation of B-cells and feeder cells, such as murine EL4-B5 feeder cells.

With the elimination of the need to use non-defined macrophage/T-cell cultivation supernatants in the co-cultivation of B-cells and feeder cells the co-cultivation process is made, amongst other things, more robust, less expensive and easily adaptable to B-cell derived from different species.

The invention is further based at least in part on the finding that when employing phorbol myristate acetate in combination with synthetic cytokines and synthetic interleukins the concentrations of each of these components has to be within certain ranges in order to ensure a positive effect.

Immunization

For the generation of therapeutic antibodies either a non-human animal is immunized with the therapeutic target (either alone or in combination with an immunogenic stimulus) to elicit an immune response or synthetic approaches, such as phage display libraries are used. If a transgenic animal (i.e. having a human immune system) or a human phage display library is used human antibodies are obtained. Otherwise non-human animal antibodies are obtained that will be humanized thereafter. A rare possibility to obtain potential therapeutic antibodies is from the blood of a human being that has recovered from a disease.

Often non-human animals, such as mice, rabbits, hamster and rats, are used as animal model for evaluating antibody based therapies. Therefore, it is normally required to provide cross-reactive antibodies binding to the non-human animal antigen as well as to the human antigen.

In the method as reported herein B-cells obtained from any source e.g. human, mouse, hamster or rabbit, can be used. Depending on the source of the B-cell the feeder cells and the feeder mix are adjusted/chosen.

In case of a rabbit B-cell the feeder cell is either an EL4-B5 cell or a mammalian cell, such as a CHO cell or a BHK cell or a HEK cell, expressing rabbit CD40L. In one embodiment the rabbit is selected from New Zealand White (NZW) rabbits, Zimmermann-rabbits (ZIKA), Alicia-mutant strain rabbits, basilea mutant strain rabbits, transgenic rabbits with a human immunoglobulin locus, rbIgM knockout rabbits, and cross-breeding thereof.

In case of a human B-cell the feeder cell is either an EL4-B5 cell or a mammalian cell, such as a CHO cell or a BHK cell or a HEK cell, expressing human CD40L.

In case of a murine B-cell the feeder cell is either an EL4-B5 cell or a mammalian cell, such as a CHO cell or a BHK cell or a HEK cell, expressing mouse CD40L. In one embodiment the mouse is an NMRI-mouse or a balb/c-mouse.

In case of a hamster B-cell the feeder cell is either an EL4-B5 cell or a mammalian cell, such as a CHO cell or a BHK cell or a HEK cell, expressing hamster CD40L. In one embodiment the hamster is selected from Armenian hamster (*Cricetulus migratorius*), Chinese hamster (*Cricetulus griseus*), and Syrian hamster (*Mesocricetulus auratus*). In one embodiment the hamster is the Armenia hamster.

Source and Isolation of B-Cells

The blood provides a high diversity of antibody producing B-cells. The therefrom obtained B-cell clones secrete antibodies that have almost no identical or overlapping amino acid sequences within the CDRs, thus, show a high diversity.

In one embodiment B-cells, e.g. from the blood or the spleen, are obtained of from 4 days after immunization until at most 14 days after immunization or the most recent boost of the non-human animal. This time span allows for a high flexibility in the method as reported herein. In this time span it is likely that the B-cells providing for the most affine antibodies migrate from spleen to blood (see e.g. Paus, D., et al., JEM 203 (2006) 1081-1091; Smith, K. G. S., et al., The EMBO J. 16 (1997) 2996-3006; Wrammert, J., et al., Nature 453 (2008) 667-672).

B-cells from the blood, e.g. of a non-human animal or from human blood, may be obtained with any method known in the art. For example, density gradient centrifugation (DGC) or red blood cell lysis (lysis) can be used. Density gradient centrifugation compared to hypotonic lysis provides for a higher overall yield, i.e. number of B-cell clones. Additionally from the cells obtained by density gradient centrifugation a larger number of cells divides and grows in the co-cultivation step. Also the concentration of secreted antibody is higher compared to cells obtained with a different method. Therefore, in one embodiment the providing of a population of B-cells is by density gradient centrifugation.

Selection Steps Prior to Co-Cultivation

B-cells producing antibodies that specifically bind an antigen can be enriched from peripheral blood mononuclear cells (PBMCs). Thus, in one embodiment of all methods as reported herein the B-cell population is enriched from peripheral blood mononuclear cells (PBMCs).

In one embodiment of all methods as reported herein the PBMCs are depleted of macrophages. This is advantageous for B-cells of rabbit origin for the co-cultivation step.

Macrophages can be depleted from PBMCs by adhesion to the surface of the cell culture plate (see pre-incubation step).

Incubating the population of B-cells in co-cultivation medium prior to the single cell depositing increases the total number of antibody secreting cells obtained after the single cell depositing compared to a single cell depositing directly after the isolation and optional enrichment of the population of B-cells from the blood of a non-human animal (in one embodiment the non-human animal is a rabbit). Specifically the incubating is at about 37° C. for about one hour in EL-4 B5 medium, e.g. using a cell culture incubator.

In one embodiment of the methods as reported herein the cells are from a protein-immunized animal and are depleted of macrophages prior to the labeling.

Cells not producing an antibody binding the antigen or, likewise, cells producing an antibody binding to the antigen can be reduced or enriched, respectively, by using a panning approach. Therein the respective antigen is presented attached to a surface and cells binding thereto are selectively enriched in the cell population in case the bound cells are processed further, or reduced in the cell population in case the cells remaining in solution are processed further.

The method as reported herein comprises in one embodiment prior to the single cell depositing a selecting step in which B-cells producing specific and/or non-cross-reactive antibodies are selected based on cell surface markers and fluorescence activated cell sorting/gating. In one embodiment mature B-cells are sorted/enriched/selected. For selection of B-cells from different non-human animal species different cell surface markers can be used.

With the labeling of non-target cell populations and non-specifically binding lymphocytes it is possible to selectively deplete these cells. In this depletion step only a partial depletion can be achieved. Albeit the depletion is not quantitative it provides for an advantage in the succeeding fluorescence labeling of the remaining cells as the number of interfering cells can be reduced or even minimized. By a single cell depositing of mature B-cells (memory B-cells, affinity matured plasmablasts and plasma cells) by fluorescence activated cell sorting using the labeling a higher number of IgG$^+$-wells/cell clones can be obtained in the co-cultivation step.

Different cell populations can be labeled by using different surface markers such as CD3$^+$-cells (T-cells), CD119$^+$-cells (B-cells), IgM$^+$-cells (mature naive B-cells), IgG$^+$-cells (mature B-cells), LC$^+$-cells, CD38$^+$-cells (e.g. plasmablasts), and IgG$^+$CD38$^+$-cells (pre-plasma cells).

Immuno-fluorescence labeling for selection of mature IgG$^+$-B-cells, such as memory B-cells, plasmablasts, and plasma cells, is available. For a selection or enrichment of B-cells the cells are either single labeled or double labeled, or triple labeled. Also required is a labeling that results in about 0.1% to 2.5% of labeled cells of the total cell population.

In one embodiment B-cells are deposited as single cells selected by the labeling of surface molecules present on 0.1% to 2.5% of the B-cells in the population, in another embodiment on 0.3% to 1.5% of the B-cells of the population, in a further embodiment on 0.5% to 1% of the B-cells of the population.

TABLE

Immuno-fluorescence labeling for the determination of mature mouse-, hamster- and rabbit-B-cells.

| B-cell origin | sorting of B-cells with | fraction of all viable cells (%) |
|---|---|---|
| mouse | IgG$^+$CD19$^+$ | 0.5 ± 0.2 n = 14 |
| mouse | IgG$^+$CD38$^+$ | 0.8 ± 0.5 n = 9 |
| mouse | IgG$^+$CD138$^+$ | 0.06 ± 0.07 n = 6 |
| mouse | IgG$^-$CD138$^+$ | 0.6 ± 0.5 n = 6 |
| mouse | IgG$^+$CD27$^+$ | 0.1 ± 0.1 n = 8 |
| mouse | CD27$^+$CD138$^+$ | 1.5 ± 0.5 n = 2 |
| mouse | CD27$^+$IgG$^+$CD3$^-$ | 0.10 ± 0.04 n = 3 |
| mouse | CD3$^-$CD27$^+$ | 1.33 n = 1 |
| mouse | IgG$^+$CD268$^+$ | 0.8 n = 1 |
| mouse | CD38$^+$CD3$^-$ | 12 ± 7 n = 2 |
| hamster | IgG$^+$IgM$^-$ | 0.6 ± 0.1 n = 15 |
| rabbit | IgG$^+$ | 0.6 ± 0.2, n = 5 |
| rabbit | IgG$^+$IgM$^-$ | 0.4 ± 0.2, n = 2 |
| rabbit | IgG$^+$CD138$^+$ | 0.3 ± 0.1, n = 5 |

In one embodiment the methods comprise the step of depleting the B-cell population of macrophages and enriching of B-cells of the B-cell population secreting antibody specifically binding a target antigen.

Single Cell Depositing

The method as reported herein comprises the step of depositing the B-cells of a B-cell population as single cells. In one embodiment of all methods as reported herein the depositing as single cells is by fluorescence activated cell sorting (FACS). The surface marker used for the labeling required for the FACS single cell depositing can be with the specific marker combination as outlined herein.

An additional centrifugation step after the single cell depositing and prior to the co-cultivation increases the number of antibody secreting cells and increases the amount of the secreted IgG.

In one embodiment of all methods as reported herein the method comprises the step of centrifuging the single deposited cells prior to the co-cultivation. In one preferred embodiment the centrifuging is for 5 min. at 300×g.

Co-Cultivation

The single deposited B-cells are co-cultivated with feeder cells in the presence of a synthetic feeder mix as reported herein.

In one embodiment the B-cells are co-cultivated with murine EL-4 B5 cells as feeder cells.

As outlined above an increase in the yield in the co-cultivation step (number of IgG$^+$-wells/cell clones as well as IgG-concentration) and also an enrichment or isolation of mature IgG$^+$-B-cell from PBMCs can be achieved by suitable immuno fluorescence labeling.

The single cell depositing of IgG$^+$IgM$^-$-cells can be used for B-cells of immunized and non-immunized non-human animals.

The single cell depositing of IgG$^+$-, and/or IgG$^+$CD138$^+$-, and/or CD138$^+$- and/or IgG$^+$IgM$^-$-B-cells, and/or IgG$^+$LC$^+$-, and/or IgG$^+$CD138$^+$LC$^+$-, and/or CD138$^+$LC$^+$- and/or IgG$^+$IgM$^-$LC$^+$-B-cells can be used for rabbit-B-cells.

The immuno-fluorescence labeling used for B-cells obtained from the blood of an experimental non-human animal can also be used for the labeling of B-cells obtained from the spleen and other immunological organs of an experimental non-human animal, such as mouse, hamster and rabbit. For rabbit-blood derived B-cells 0.2% of IgG$^+$-cells were found after depletion of macrophages. Peyer'sche plaques from rabbit showed 0.4% of IgG$^+$-cells and spleen showed 0.3% of IgG$^+$-cells after depletion of macrophages.

With the methods as reported herein after about seven (7) days, i.e. after 5, 6, 7, or 8 days, especially after 7 or 8 days, of co-cultivation sufficient antibody concentrations can be obtained. With the thereby provided amount of antibody a high number of different analyses can be performed in order to characterize the antibody, e.g. regarding binding specificity, in more detail. With the improved characterization of the antibody at this early stage in the screening/selection process it is possible to reduce the number of required nucleic acid isolations and sequencing reactions that have to be performed. Additionally the B-cell clone provides an amount of mRNA encoding monoclonal light and heavy chain variable region allowing the use of degenerated PCR primer and obviates the requirement of highly specific primer. Also the required number of PCR cycles is reduced. Thus, in one embodiment the reverse transcriptase PCR is with degenerated PCR primer for the light and heavy chain variable domain.

The co-cultivation step with feeder cells can be preceded and also succeeded by a number of additional steps.

Due to the origin of the feeder mix as cultivation supernatant, i.e. its production from the supernatant of cultivated thymocytes (thymocyte cultivation supernatant—TSN), considerable batch to batch variations occur.

TSN is needed in combination with feeder cells to stimulate the (single deposited) B-cell, thereby inducing proliferation and antibody secretion.

In order to overcome this variability a synthetic feeder mix having the same or comparable stimulation properties can be employed.

The B-cell-species-specific additives for the synthetic feeder mix result in increased amounts of secreted antibody by the respective B-cell clone. Concomitantly highly producing cells contain more mRNA which in turn facilitates the reverse transcription and sequencing of the encoding nucleic acid, e.g. with a redundant, non-specific primer set.

The co-cultivation is in one embodiment of all methods as reported herein in polystyrene multi well plates with wells with a round bottom. The working volume of the wells is in one embodiment of all methods as reported herein of 50 μl to 250 μl. In one embodiment the wells are coated at least partially with a non-fibrous substrate prepared from a blend of polymer plastic resin and amphipathic molecules, wherein the amphipathic molecule comprises a hydrophilic moiety and a hydrophobic region, wherein the hydrophobic regions are anchored within the substrate and the hydrophilic moieties are exposed on the substrate. In one embodiment the amphipathic molecules are chosen from alkylamine ethoxylated, poly (ethylene imine), octyldecamine or mixtures thereof (see e.g. EP 1 860 181).

Characterization of Co-Cultivated Cells

For the (qualitative and quantitative) determination of secreted IgG after the co-cultivation generally all methods known to a person of skill in the art such as an ELISA can be used. In one embodiment of all methods as reported herein an ELISA is used.

Depending on the characterization results a B-cell clone can be obtained, i.e. selected. The term "clone" denotes a population of dividing and antibody secreting B-cells arising from/originating from a single B-cell. Thus, a B-cell clone produces a monoclonal antibody.

Isolation of mRNA, Cloning and Sequencing

From the B-cells the total mRNA can be isolated and transcribed in cDNA. With specific primers the cognate VH- and VL-region encoding nucleic acid can be amplified. Almost no identical sequences are obtained. The method provides for highly diverse antibodies binding to the same antigen.

The primers used for the amplification of the VH-encoding nucleic acid can be used for cDNA obtained from cells from the NMRI-mouse, the Armenian Hamster, the Balb/c-mouse as well as the Syrian hamster and the rabbit.

In one embodiment of all methods as reported herein the amino acid sequence is derived from the amplified VH-encoding nucleic acid and the exact start and end point is identified by locating the amino acid sequences of EVQL/QVQL to VSS (VH-region) and DIVM/DIQM to KLEIK (VL-region).

Also reported herein is a method for producing an antibody comprising the following steps:

a) providing a population of (mature) B-cells (obtained from the blood of an experimental non-human animal), b) staining the cells of the population of B-cells with at least one fluorescence dye (in one embodiment with one to three, or two to three fluorescence dyes), c) depositing single cells of the stained population of B-cells in individual containers (in one embodiment is the container a well of a multi well plate), d) cultivating the deposited individual B-cells in the presence of feeder cells and a feeder mix (in one embodiment the feeder cells are EL-4 B5 cells, in one embodiment the feeder mix is the synthetic feeder mix as reported herein), e) determining the binding specificity of the antibodies secreted in the cultivation of the individual B-cells, f) determining the amino acid sequence of the variable light and heavy chain domain of specifically binding antibodies by a reverse transcriptase PCR and nucleotide sequencing, and thereby obtaining a monoclonal antibody variable light and heavy chain domain encoding nucleic acid, g) introducing the monoclonal antibody light and heavy chain variable domain encoding nucleic acid in an expression cassette for the expression of an antibody, h) introducing the nucleic acid in a cell, i) cultivating the cell and recovering the antibody from the cell or the cell culture supernatant and thereby producing an antibody.

In one embodiment the non-human animal is selected from rat, mouse, hamster, rabbit, non-human primates, sheep, dog, cow, chicken, amphibians, and reptiles.

The Method as Reported Herein

Herein is reported a method for the co-cultivation of single deposited B-cells, which can be of any source, with feeder cells in a suitable co-cultivation medium, wherein all cell growth stimulating additives are of synthetic origin.

The invention is based at least in part on the finding that phorbol myristate acetate alone or a combination of phorbol myristate acetate (PMA) with synthetic cytokines and synthetic interleukins can replace the commonly employed macrophage/T-cell cultivation supernatant used in the co-cultivation of B-cells and feeder cells, such as murine EL4-B5 feeder cells.

The invention is further based at least in part on the finding that when employing phorbol myristate acetate in combination with synthetic cytokines and synthetic interleukins the concentrations of each of these components has to be within certain ranges in order to ensure a positive effect.

One aspect as reported herein is a method for co-cultivating one or more B-cells (for the production of immunoglobulin) comprising the step of co-cultivating the one or more B-cells with feeder cells in the presence of phorbol myristate acetate (PMA) (and thereby producing immunoglobulin).

In one embodiment the co-cultivating is in the presence of 1.5-7.25 ng/ml phorbol myristate acetate.

One aspect as reported herein is a method for co-cultivating one or more B-cells (for the production of immunoglobulin) comprising the step of co-cultivating the one or more B-cells with feeder cells in the presence of phorbol myristate acetate (PMA), IL-1beta, TNFalpha, IL-2, IL-10 and IL-6 (and thereby producing immunoglobulin).

In one embodiment the co-cultivating is in the presence of
about 0.3-3 ng/ml phorbol myristate acetate,
about 0.02-0.2 ng/ml IL-1beta,
about 0.02-0.2 ng/ml TNFalpha,
about 0.5-5 ng/ml IL-2,
about 0.1-1 ng/ml IL-10, and
about 0.1-1 ng/ml IL-6.

In one embodiment the co-cultivating is in the presence of
about 0.3-3 ng/ml phorbol myristate acetate,
about 0.064 ng/ml IL-1beta,
about 0.064 ng/ml TNFalpha,
about 1.6 ng/ml IL-2,
about 0.32 ng/ml IL-10, and
about 0.32 ng/ml IL-6.

In one embodiment the co-cultivating is in the presence of
about 0.9-3 ng/ml phorbol myristate acetate,
about 0.02-0.2 ng/ml IL-1beta,
about 0.02-0.2 ng/ml TNFalpha,
about 0.5-5 ng/ml IL-2,
about 0.1-1 ng/ml IL-10, and
about 0.1-1 ng/ml IL-6.

In one embodiment the co-cultivating is in the presence of
about 0.9-3 ng/ml phorbol myristate acetate,
about 0.064 ng/ml IL-1beta,
about 0.064 ng/ml TNFalpha,
about 1.6 ng/ml IL-2,
about 0.32 ng/ml IL-10, and
about 0.32 ng/ml IL-6.

In one embodiment the co-cultivating is in the presence of
about 0.9-3 ng/ml phorbol myristate acetate,
about 0.02 ng/ml IL-1beta,
about 0.02 ng/ml TNFalpha,
about 0.5 ng/ml IL-2,
about 0.1 ng/ml IL-10, and
about 0.1 ng/ml IL-6.

In one embodiment the co-cultivating is in the presence of
about 0.5-2.5 ng/ml phorbol myristate acetate,
about 0.02-0.2 ng/ml IL-1beta,
about 0.02-0.2 ng/ml TNFalpha,
about 0.5-5 ng/ml IL-2,
about 0.1-1 ng/ml IL-10, and
about 0.1-1 ng/ml IL-6.

In one embodiment the co-cultivating is in the presence of
about 0.5-2.5 ng/ml phorbol myristate acetate,
about 0.064 ng/ml IL-1beta,
about 0.064 ng/ml TNFalpha,
about 1.6 ng/ml IL-2,
about 0.32 ng/ml IL-10, and
about 0.32 ng/ml IL-6.

In one embodiment the co-cultivating is in the presence of
about 0.2-0.35 ng/ml phorbol myristate acetate,
about 0.02-0.2 ng/ml IL-1beta,
about 0.02-0.2 ng/ml TNFalpha,
about 0.5-5 ng/ml IL-2,
about 0.1-1 ng/ml IL-10, and
about 0.1-1 ng/ml IL-6.

In one embodiment the co-cultivating is in the presence of
about 0.2-0.35 ng/ml phorbol myristate acetate,
about 0.064 ng/ml IL-1beta,
about 0.064 ng/ml TNFalpha,
about 1.6 ng/ml IL-2,
about 0.32 ng/ml IL-10, and
about 0.32 ng/ml IL-6.

In one embodiment the co-cultivating is in the presence of
about 0.05-0.7 ng/ml phorbol myristate acetate,
about 0.02-0.2 ng/ml IL-1beta,
about 0.02-0.2 ng/ml TNFalpha,
about 0.5-5 ng/ml IL-2,
about 0.1-1 ng/ml IL-10, and
about 0.1-1 ng/ml IL-6.

In one embodiment the co-cultivating is in the presence of
about 0.05-0.7 ng/ml phorbol myristate acetate,
about 0.2 ng/ml IL-1beta,
about 0.2 ng/ml TNFalpha,
about 5 ng/ml IL-2,
about 1 ng/ml IL-10, and
about 1 ng/ml IL-6.

In one embodiment the co-cultivating is in the presence of
about 0.05-0.7 ng/ml phorbol myristate acetate,
about 0.064 ng/ml IL-1beta,
about 0.064 ng/ml TNFalpha,
about 1.6 ng/ml IL-2,
about 0.32 ng/ml IL-10, and
about 0.32 ng/ml IL-6.

In one preferred embodiment the co-cultivating is in the presence of about 1.3 ng/ml phorbol myristate acetate, about 0.064 ng/ml IL-1beta, about 0.064 ng/ml TNFalpha, about 1.6 ng/ml IL-2, about 0.32 ng/ml IL-10, and about 0.32 ng/ml IL-6.

In one preferred embodiment the co-cultivating is in the presence of about 0.9 ng/ml phorbol myristate acetate, about 0.02 ng/ml IL-1beta, about 0.02 ng/ml TNFalpha, about 0.5 ng/ml IL-2, about 0.1 ng/ml IL-10, and about 0.1 ng/ml IL-6.

In one embodiment the amount of phorbol myristate acetate (PMA) used in the co-cultivation is given by weight and the amount of IL-1beta, TNFalpha, IL-2, IL-10 and IL-6 used in the co-cultivation is given by activity.

In one embodiment the co-cultivating is in the presence of about 0.3-3 ng/ml phorbol myristate acetate, about 0.02-0.2 ng/ml with $5.5\text{-}14*10^8$ IU/mg (murine) IL-1beta, about 0.02-0.2 ng/ml with $2.3\text{-}2.9*10^8$ U/mg (murine) TNFalpha, about 0.5-5 ng/ml with 6-7 (preferably 6.3)$*10^6$ IU/mg (murine) IL-2, about 0.1-1 ng/ml with $6\text{-}7.5*10^5$ IU/mg (murine) IL-10, and about 0.1-1 ng/ml with $9.2\text{-}16.1*10^8$ U/mg (murine) IL-6.

In one embodiment the co-cultivating is in the presence of about 0.3-3 ng/ml phorbol myristate acetate, about 0.064 ng/ml with $5.5\text{-}14*10^8$ IU/mg (murine) IL-1beta, about 0.064 ng/ml with $2.3\text{-}2.9*10^8$ U/mg (murine) TNFalpha, about 1.6 ng/ml with 6-7 (preferably 6.3)$*10^6$ IU/mg (murine) IL-2, about 0.32 ng/ml with $6\text{-}7.5*10^5$ IU/mg (murine) IL-10, and about 0.32 ng/ml with $9.2\text{-}16.1*10^8$ U/mg (murine) IL-6.

In one embodiment the co-cultivating is in the presence of about 0.9-3 ng/ml phorbol myristate acetate, about 0.02-0.2 ng/ml with $5.5\text{-}14*10^8$ IU/mg (murine) IL-1beta, about 0.02-0.2 ng/ml with $2.3\text{-}2.9*10^8$ U/mg (murine) TNFalpha, about 0.5-5 ng/ml with 6-7 (preferably 6.3)$*10^6$ IU/mg (murine) IL-2, about 0.1-1 ng/ml with $6\text{-}7.5*10^5$ IU/mg (murine) IL-10, and about 0.1-1 ng/ml with $9.2\text{-}16.1*10^8$ U/mg (murine) IL-6.

In one embodiment the co-cultivating is in the presence of about 0.9-3 ng/ml phorbol myristate acetate, about 0.064 ng/ml with $5.5\text{-}14*10^8$ IU/mg (murine) IL-1beta, about 0.064 ng/ml with $2.3\text{-}2.9*10^8$ U/mg (murine) TNFalpha, about 1.6 ng/ml with 6-7 (preferably 6.3)$*10^6$ IU/mg (murine) IL-2, about 0.32 ng/ml with $6\text{-}7.5*10^5$ IU/mg (murine) IL-10, and about 0.32 ng/ml with $9.2\text{-}16.1*10^8$ U/mg (murine) IL-6.

In one embodiment the co-cultivating is in the presence of about 0.9-3 ng/ml phorbol myristate acetate, about 0.02 ng/ml with $5.5\text{-}14*10^8$ IU/mg (murine) IL-1beta, about 0.02 ng/ml with $2.3\text{-}2.9*10^8$ U/mg (murine) TNFalpha, about 0.5 ng/ml with 6-7 (preferably 6.3)$*10^6$ IU/mg (murine) IL-2, about 0.1 ng/ml with $6\text{-}7.5*10^5$ IU/mg (murine) IL-10, and about 0.1 ng/ml with $9.2\text{-}16.1*10^8$ U/mg (murine) IL-6.

In one embodiment the co-cultivating is in the presence of about 0.5-2.5 ng/ml phorbol myristate acetate, about 0.02-0.2 ng/ml with $5.5\text{-}14*10^8$ IU/mg (murine) IL-1beta, about 0.02-0.2 ng/ml with $2.3\text{-}2.9*10^8$ U/mg (murine) TNFalpha, about 0.5-5 ng/ml with 6-7 (preferably 6.3)$*10^6$ IU/mg (murine) IL-2, about 0.1-1 ng/ml with $6\text{-}7.5*10^5$ IU/mg (murine) IL-10, and about 0.1-1 ng/ml with $9.2\text{-}16.1*10^8$ U/mg (murine) IL-6.

In one embodiment the co-cultivating is in the presence of about 0.5-2.5 ng/ml phorbol myristate acetate, about 0.064 ng/ml with $5.5\text{-}14*10^8$ IU/mg (murine) IL-1beta, about 0.064 ng/ml with $2.3\text{-}2.9*10^8$ U/mg (murine) TNFalpha, about 1.6 ng/ml with 6-7 (preferably 6.3)$*10^6$ IU/mg (murine) IL-2, about 0.32 ng/ml with $6\text{-}7.5*10^5$ IU/mg (murine) IL-10, and about 0.32 ng/ml with $9.2\text{-}16.1*10^8$ U/mg (murine) IL-6.

In one embodiment the co-cultivating is in the presence of about 0.2-0.35 ng/ml phorbol myristate acetate, about 0.02-0.2 ng/ml with $5.5\text{-}14*10^8$ IU/mg (murine) IL-1beta, about 0.02-0.2 ng/ml with $2.3\text{-}2.9*10^8$ U/mg (murine) TNFalpha, about 0.5-5 ng/ml with 6-7 (preferably 6.3)$*10^6$ IU/mg (murine) IL-2, about 0.1-1 ng/ml with $6\text{-}7.5*10^5$ IU/mg (murine) IL-10, and about 0.1-1 ng/ml with $9.2\text{-}16.1*10^8$ U/mg (murine) IL-6.

In one embodiment the co-cultivating is in the presence of about 0.2-0.35 ng/ml phorbol myristate acetate, about 0.064 ng/ml with $5.5\text{-}14*10^8$ IU/mg (murine) IL-1beta about 0.064 ng/ml with $2.3\text{-}2.9*10^8$ U/mg (murine) TNFalpha, about 1.6 ng/ml with 6-7 (preferably 6.3)$*10^6$ IU/mg (murine) IL-2, about 0.32 ng/ml with $6\text{-}7.5*10^5$ IU/mg (murine) IL-10, and about 0.32 ng/ml with $9.2\text{-}16.1*10^8$ U/mg (murine) IL-6.

In one embodiment the co-cultivating is in the presence of about 0.05-0.7 ng/ml phorbol myristate acetate, about 0.02-0.2 ng/ml with $5.5\text{-}14*10^8$ IU/mg (murine) IL-1beta, about 0.02-0.2 ng/ml with $2.3\text{-}2.9*10^8$ U/mg (murine) TNFalpha, about 0.5-5 ng/ml with 6-7 (preferably 6.3)$*10^6$ IU/mg (murine) IL-2, about 0.1-1 ng/ml with $6\text{-}7.5*10^5$ IU/mg (murine) IL-10, and about 0.1-1 ng/ml with $9.2\text{-}16.1*10^8$ U/mg (murine) IL-6.

In one embodiment the co-cultivating is in the presence of about 0.05-0.7 ng/ml phorbol myristate acetate, about 0.2 ng/ml with $5.5\text{-}14*10^8$ IU/mg (murine) IL-1beta, about 0.2 ng/ml with $2.3\text{-}2.9*10^8$ U/mg (murine) TNFalpha, about 5 ng/ml with 6-7 (preferably 6.3)$*10^6$ IU/mg (murine) IL-2, about 1 ng/ml with $6\text{-}7.5*10^5$ IU/mg (murine) IL-10, and about 1 ng/ml with $9.2\text{-}16.1*10^8$ U/mg (murine) IL-6.

In one embodiment the co-cultivating is in the presence of about 0.05-0.7 ng/ml phorbol myristate acetate, about 0.064 ng/ml with $5.5\text{-}14*10^8$ IU/mg (murine) IL-1beta, about 0.064 ng/ml with $2.3\text{-}2.9*10^8$ U/mg (murine) TNFalpha, about 1.6 ng/ml with 6-7 (preferably 6.3)$*10^6$ IU/mg (murine) IL-2, about 0.32 ng/ml with $6\text{-}7.5*10^5$ IU/mg (murine) IL-10, and about 0.32 ng/ml with $9.2\text{-}16.1*10^8$ U/mg (murine) IL-6.

In one preferred embodiment the co-cultivating is in the presence of about 1.3 ng/ml phorbol myristate acetate, about 0.064 ng/ml with $5.5\text{-}14*10^8$ IU/mg (murine) IL-1beta, about 0.064 ng/ml with $2.3\text{-}2.9*10^8$ U/mg (murine) TNFalpha, about 1.6 ng/ml with 6-7 (preferably 6.3)$*10^6$ U/mg (murine) IL-2, about 0.32 ng/ml with $6\text{-}7.5*10^5$ IU/mg (murine) IL-10, and about 0.32 ng/ml with $9.2\text{-}16.1*10^8$ U/mg (murine) IL-6.

In one preferred embodiment the co-cultivating is in the presence of about 0.9 ng/ml phorbol myristate acetate, about 0.02 ng/ml with $5.5\text{-}14*10^8$ IU/mg (murine) IL-1beta, about 0.02 ng/ml with $2.3\text{-}2.9*10^8$ U/mg (murine) TNFalpha, about 0.5 ng/ml with 6-7 (preferably 6.3)$*10^6$ IU/mg (murine) IL-2, about 0.1 ng/ml with $6\text{-}7.5*10^5$ IU/mg (murine) IL-10, and about 0.1 ng/ml with $9.2\text{-}16.1*10^8$ U/mg (murine) IL-6.

In one embodiment the feeder cells are EL-4 B5 cells.

In one embodiment the method is for the co-cultivation of one B-cell. In one preferred embodiment the one B-cell is a single deposited B-cell.

In one embodiment the co-cultivating is further in the presence of *Staphylococcus aureus* strain Cowans cells (SAC).

In one embodiment the incubating is for 5 to 14 days.

In all methods as reported herein the co-cultivation is in the absence of a thymocyte cultivation supernatant. Thus, the added feeder mix is not a cultivation supernatant.

In one embodiment neither of a thymocyte cultivation supernatant, a macrophage cultivation supernatant, or a T-cell cultivation supernatant is added to the cultivation.

One additional aspect as reported herein is a feeder mix comprising (consisting of) about 2 ng/ml (murine) IL-1beta, about 2 ng/ml (murine) TNFalpha, about 50 ng/ml (murine) IL-2, about 10 ng/ml (murine) IL-10 and about 10 ng/ml (murine) IL-6.

One additional aspect as reported herein is the use of a (synthetic) feeder mix comprising (consisting of) about 2 ng/ml (murine) IL-1beta, about 2 ng/ml (murine) TNFalpha, about 50 ng/ml (murine) IL-2, about 10 ng/ml (murine)

IL-10 and about 10 ng/ml (murine) IL-6 in the co-cultivation of (murine) EL-4 B5 cells with (single deposited) human, murine or rabbit B-cells.

When using a synthetic feeder mix comprising about 2 ng/ml (murine) IL-1beta, about 2 ng/ml (murine) TNFalpha, about 50 ng/ml (murine) IL-2, about 10 ng/ml (murine) IL-10 and about 10 ng/ml (murine) IL-6 in the co-cultivation of (murine) EL4-B5 cells with (single deposited) (rabbit) B-cells the frequency of IgG positive wells is comparable with that when TSN is used.

TABLE

| | TSN | 2 ng/ml IL-1beta<br>2 ng/ml TNFalpha<br>50 ng/ml mIL-2<br>10 ng/ml mIL-10<br>10 ng/ml mIL-6 |
|---|---|---|
| IgG positive wells [% of total wells] | 64.9 | 58.3 |

Also the average productivity is comparable with that when TSN is used (see following Table).

TABLE

| | TSN | 2 ng/ml IL-1beta<br>2 ng/ml TNFalpha<br>50 ng/ml mIL-2<br>10 ng/ml mIL-10<br>10 ng/ml mIL-6 |
|---|---|---|
| average IgG productivity [µg/ml] | 3.2 | 2.6 |

When adding PMA (3 ng/ml) in addition to the synthetic feeder mix then the results are significantly different (see following Table).

TABLE

| | 2 ng/ml IL-1beta<br>2 ng/ml TNFalpha<br>50 ng/ml mIL-2<br>10 ng/ml mIL-10<br>10 ng/ml mIL-6<br>SAC | 2 ng/ml IL-1beta<br>2 ng/ml TNFalpha<br>50 ng/ml mIL-2<br>10 ng/ml mIL-10<br>10 ng/ml mIL-6<br>SAC<br>3 ng/ml PMA |
|---|---|---|
| IgG positive wells [% of total wells] | 63.1 | 2.7 |
| average IgG productivity [µg/ml] | 2.1 | 0.07 |

It has been found that when employing phorbol myristate acetate in combination with synthetic cytokines and synthetic interleukins the concentrations of each of these components has to be within certain ranges in order to ensure a synergistic effect.

The synthetic feeder mix comprising 2 ng/ml (murine) IL-1beta, 2 ng/ml (murine) TNFalpha, 50 ng/ml (murine) IL-2, 10 ng/ml (murine) IL-10 and 10 ng/ml (murine) IL-6 is termed in the following Table 1×CM.

Thus, a 0.1×CM feeder mix as in the following Table corresponds to a synthetic feeder mix comprising 0.2 ng/ml (murine) IL-1beta, 0.2 ng/ml (murine) TNFalpha, 5 ng/ml (murine) IL-2, 1 ng/ml (murine) IL-10 and 1 ng/ml (murine) IL-6.

It has surprisingly been found that in the presence of PMA the concentration of the synthetic feeder mix can be reduced without impairing with the increased number of IgG positive wells as well as increased productivity. At the same time the cells are not over-stimulated and thereby abrogating the positive effect.

It has also surprisingly been found that by using PMA alone, i.e. in the absence of cytokines and interleukins, comparable numbers of IgG positive wells and even increased productivity can be achieved.

Number of IgG positive wells [% of total]:

| | CM | | | | | | | |
|---|---|---|---|---|---|---|---|---|
| PMA | 2x | 1.1x | 1x | 0.32x | 0.1x | 0.032x | 0.01x | 0x |
| 3 ng/ml | n.d. | n.d. | 13.1 | 13.1 | 35.7 | 72.6 | 69.0 | n.d. |
| 0.95 ng/ml | n.d. | n.d. | 8.3 | 23.8 | 50.0 | 67.9 | 69.0 | 28.6 |
| 0.3 ng/ml | n.d. | n.d. | 17.9 | 57.1 | 67.9 | 70.2 | 69.0 | n.d. |
| 0.095 ng/ml | n.d. | n.d. | 38.1 | n.d. | n.d. | n.d. | n.d. | n.d. |
| 0 ng/ml | 23.8 | 36.9 | 27.4 | 46.4 | 50.0 | 36.9 | 41.7 | n.d. | n.d. = not determined

Average IgG productivity [µg/ml]:

| | CM | | | | | | | |
|---|---|---|---|---|---|---|---|---|
| PMA | 2x | 1.1x | 1x | 0.32x | 0.1x | 0.032x | 0.01x | 0x |
| 3 ng/ml | n.d. | n.d. | 0.351 | 0.125 | 0.363 | 3.480 | 3.893 | n.d. |
| 0.95 ng/ml | n.d. | n.d. | 0.100 | 0.134 | 1.623 | 5.340 | 4.235 | 1.650 |
| 0.3 ng/ml | n.d. | n.d. | 0.720 | 2.662 | 4.450 | 3.476 | 1.931 | n.d. |
| 0.095 ng/ml | n.d. | n.d. | 1.390 | n.d. | n.d. | n.d. | n.d. | n.d. |
| 0 ng/ml | 0.549 | 1.496 | 0.675 | 2.233 | 1.817 | 0.928 | 0.375 | n.d. | n.d. = not determined

The number of antigen specific clones is not affected (shown in the following for B-cells obtained from a rabbit immunized with human serum albumin (HSA)).

Number of anti-HSA antibody positive wells [% of total]:

| | CM | | | | | | | |
|---|---|---|---|---|---|---|---|---|
| PMA | 2x | 1.1x | 1x | 0.32x | 0.1x | 0.032x | 0.01x | 0x |
| 3 ng/ml | n.d. | n.d. | 6.0 | 3.6 | 7.1 | 34.5 | 33.3 | n.d. |
| 0.95 ng./ml | n.d. | n.d. | 3.6 | 7.1 | 27.4 | 31.0 | 27.4 | 19.0 |
| 0.3 ng/ml | n.d. | n.d. | 3.6 | 22.6 | 28.6 | 27.4 | 28.6 | n.d. |
| 0.095 ng/ml | n.d. | n.d. | 23.8 | n.d. | n.d. | n.d. | n.d. | n.d. |
| 0 ng/ml | 6.0 | 20.2 | 3.6 | 23.8 | 26.2 | 16.7 | 17.9 | n.d. | n.d. = not determined

Number of anti-HSA antibody positive wells [% of IgG positive wells]:

| | CM | | | | | | | |
|---|---|---|---|---|---|---|---|---|
| PMA | 2x | 1.1x | 1x | 0.32x | 0.1x | 0.032x | 0.01x | 0x |
| 3 ng/ml | n.d. | n.d. | 45.5 | 27.3 | 20.0 | 47.5 | 48.3 | n.d. |
| 0.95 ng/ml | n.d. | n.d. | 42.9 | 30.0 | 54.8 | 45.6 | 39.7 | 66.7 |
| 0.3 ng/ml | n.d. | n.d. | 20.0 | 39.6 | 42.1 | 39.0 | 41.4 | n.d. |
| 0.095 ng/ml | n.d. | n.d. | 62.5 | n.d. | n.d. | n.d. | n.d. | n.d. |
| 0 ng/ml | 25.0 | 54.8 | 13.0 | 51.3 | 52.4 | 45.2 | 42.9 | n.d. | n.d. = not determined

For the conditions 0.1×CM, 0.032×CM and without CM the influence of the PMA concentration was evaluated further (relative weighting from ○ to +++++).

34

| PMA [ng/ml] | IgG+ wells [% total] | productivity IgG+ [µg/ml] | HSA+ wells [% total] | HSA+ wells [% IgG+] |
|---|---|---|---|---|
| 0.949 | ○ | ○ | ○ | + |
| 0.712 | +++ | ++ | +++ | ++++ |
| 0.534 | +++++ | +++ | +++ | +++ |
| 0.3 | +++++ | +++++ | ○ | ○ |
| 0.225 | +++++ | +++++ | +++++ | ++++ |
| 0.127 | ++ | ++++ | + | ++ |
| 0.054 | ++++ | +++ | +++ | +++ |
| 0.011 | + | + | +++ | +++++ |
| 0.002 | + | ○ | + | ++ |

| PMA [ng/ml] | IgG+ wells [% total] | productivity IgG+ [µg/ml] | HSA+ wells [% total] | HSA+ wells [% IgG+] |
|---|---|---|---|---|
| 2.25 | ++++ | ++++ | ++ | ○ |
| 1.688 | +++++ | +++++ | +++++ | + |
| 1.266 | +++ | +++++ | +++++ | ++++ |
| 0.949 | ++++ | +++++ | +++++ | +++ |
| 0.712 | ++ | +++ | + | ○ |
| 0.534 | ++ | +++ | ++ | +++ |
| 0.3 | ++++ | +++ | ++++ | +++ |
| 0.127 | ○ | + | ○ | ++ |
| 0.011 | ○ | ○ | +++ | +++++ |

| PMA [ng/ml] | IgG+ wells [% total] | productivity IgG+ [µg/ml] | HSA+ wells [% total] | HSA+ wells [% IgG+] |
|---|---|---|---|---|
| 7.106 | +++++ | ++ | ++++ | + |
| 5.331 | ++++ | +++++ | +++ | ++ |
| 3.999 | +++ | +++ | + | ○ |
| 2.251 | +++++ | +++++ | +++++ | +++ |
| 1.688 | ++ | +++ | +++++ | +++++ |
| 0.95 | + | + | ○ | +++ |
| 0.535 | ○ | ○ | + | +++++ |

Without being bound by this theory it is assumed that in order to have a robust method values within an overlapping range resulting in the best overall number of IgG-positive wells, productivity and number of antigen-specific wells are to be used.

The following examples and sequences are provided to aid the understanding of the present invention, the true scope of which is set forth in the appended claims. It is understood that modifications can be made in the procedures set forth without departing from the spirit of the invention.

EXAMPLES

Materials and Methods

Recombinant DNA Techniques

Standard methods were used to manipulate DNA as described in Sambrook, J., et al., Molecular Cloning: A Laboratory Manual, Cold Spring Harbor Laboratory Press, Cold Spring Harbor, N.Y. (1989). The molecular biological reagents were used according to the manufacturer's instructions.

Media and Buffers

Blocking buffer for ELISA comprises 1×PBS and 1% BSA.

Coating buffer for ELISA comprises 4.29 g Na2CO3*10 H2O and 2.93 g NaHCO3 add water to a final volume of 1 liter, pH 9.6 adjusted with 2 N HCl.

Ethanol-solution for RNA isolation comprises 70% Ethanol or 80% Ethanol.

FACS-buffer for immuno fluorescence staining comprises 1×PBS and 0.1% BSA.

IMDM-buffer for ELISA comprises 1×PBS, 5% IMDM and 0.5% BSA.

Incubation buffer 1 for ELISA comprises 1×PBS, 0.5% CroteinC.

Incubation buffer 2 for ELISA comprises 1×PBS, 0.5% CroteinC and 0.02% Tween 20.

Incubation buffer 3 for ELISA comprises 1×PBS, 0.1% BSA.

Incubation buffer 4 for ELISA comprises 1×PBS, 0.5% BSA, 0.05% Tween, PBS (10×), 0.01 M KH2PO4, 0.1 M Na2HPO4, 1.37 M NaCl, 0.027 M KCl, pH 7.0.

Wash buffer 1 for ELISA comprises 1×PBS, 0.05% Tween 20.

Wash buffer 2 for ELISA comprises 1×PBS, 0.1% Tween 20.

Wash buffer 3 for ELISA comprises water, 0.9% NaCl, 0.05% Tween 20.

EL-4 B5 medium comprises RPMI 1640 supplemented with 10% FCS, 2 mM Glutamine, 1% penicillin/streptomycin solution, 2 mM sodium pyruvate, 10 mM HEPES and 0.05 mM β-mercaptoethanol.

Animal Care and Immunization

The experimental animals were held according to the German animal protection law (TierSCHG) as well as according to the respective European guidelines.

NZW rabbits obtained from Charles River Laboratories International, Inc. were used for immunization. The animals were housed according to the Appendix A "Guidelines for accommodation and care of animals" in an AAALACi accredited animal facility. All animal immunization protocols and experiments were approved by the Government of Upper Bavaria (permit number 55.2-1-54-2532-90-14) and performed according to the German Animal Welfare Act and the Directive 2010/63 of the European Parliament and Council.

Generally, the antigen was solved in $K_3PO_4$ buffer pH 7.0 at a concentration of 1 mg/ml and mixed (1:1) with complete Freud's adjuvant (CFA) till generation of stabile emulsion. The rabbits received an intra dermal (i.d.) injection of 2 ml of emulsion followed by a second intra muscular (i.m.) and third subcutaneous (s.c.) injection each with 1 ml in one week interval. The fourth i.m. injection of 1 ml was performed two weeks later followed by two further s.c. injections of 1 ml in four weeks interval.

During the immunization serum antibody titer was determined with an antigen specific assay. At an antibody titer with an $IC_{50}$ of 1:10000 the blood or the spleen of the immunized animal was removed. For reactivation of antigen specific B-cells 30 μg to 50 μg of the antigen was applied intravenously to the experimental animal three days prior to the removal of the blood or the spleen.

In more detail, NZW rabbits, 12-16 weeks old, were immunized with 400 μg recombinant human serum albumin protein (HSA; CAS RN 70024-90-7; Sigma), emulsified with complete Freund's adjuvant, at day 0 by intradermal application, followed by 200 μg HSA emulsified with complete or incomplete Freund's adjuvant at weeks 1, 2, 6, 10 and 23, by alternating intramuscular and subcutaneous injections.

Removal of Organs, Blood and Macrophages

Generally, blood from rabbits was obtained by punctuation of the ear vein or, for larger volumes, of the ear artery. Whole blood (10 ml) was collected from rabbits 4-6 days after the third, fourth, fifth and sixth immunization and used for single cell sorting by FACS.

Specifically, blood (10% of estimated total blood volume) was taken at days 4, 5 and 6 post immunizations, starting from the 3rd immunization onwards. Serum was prepared for immunogen-specific IgG titer determination by ELISA, and peripheral mononuclear cells were isolated, which were used as a source of antigen-specific B cells in the B cell cloning process.

Macrophages were isolated from the obtained blood by attachment to cell culture plastic.

EDTA containing whole blood was diluted twofold with 1×PBS before density centrifugation on lymphocyte mammal (Cedarlane Laboratories) or Ficoll Paque Plus (GE Healthcare, cat. #17-1440-03), which was performed to isolate rabbit PBMC. PBMCs were washed twice before staining with antibodies.

Density Gradient Centrifugation

The isolation of peripheral blood mononuclear cells (PBMCs) was effected by density gradient separation with Lympholyte® according to manufacturer's instructions A (Lympholyte®-mammal, Cedarlane).

Withdrawn blood was diluted 2:1 with phosphate buffered saline (PBS). In a centrifuge vial the same volume of density separation medium was provided and the diluted blood is carefully added via the wall of the vial. The vial was centrifuged for 20 min. at 800×g without braking. The lymphocytes were obtained from the white interim layer. The removed cells were supplemented with 10 ml PBS and centrifuged at 800×g for 10 min. The supernatant was discarded and the pellet was resuspended, washed, centrifuged. The final pellet was resuspended in PBS or medium.

Depletion of Macrophages

Sterile 6-well plates (cell culture grade) were used to deplete macrophages and monocytes through unspecific adhesion. Wells were either uncoated, coated with KLH (keyhole limpet haemocyanine) or with streptavidin. Each well was filled with 3 ml to (at maximum) 4 ml medium and up to 6×10⁶ peripheral blood mononuclear cells from the immunized rabbit and allowed to bind for 60 to 90 min. at 37° C. in the incubator. Thereafter the lymphocyte containing supernatant was transferred to a centrifugation vial and centrifuged at 800×g for 10 min. The pellet was resuspended in PBS or medium.

Enrichment of Antigen-Specific B-Cells

The respective antigen was diluted with coating buffer to a final concentration of 2 μg/ml. 3 ml of this solution were added to the well of a 6-well multi well plate and incubated over night at room temperature. Prior to use the supernatant was removed and the wells were washed twice or thrice with PBS. The B-cell solution was adjusted to a cell density of 2×10⁶ cells/ml and 3 ml are added to each well (up to 6×10⁶ cells per 3-4 ml medium) of a 6-well multi well plate. The plate was incubated for 60 to 90 min. at 37° C. The supernatant was removed and non-adherent cells were removed by carefully washing the wells 1-4 times with 1×PBS. For recovery of the sticky antigen-specific B-cells 1 ml of a trypsin/EDTA-solution was added to the wells of the multi well plate and incubated for 5 to 15 min. at 37° C. The incubation was stopped by addition of medium and the supernatant was transferred to a centrifugation vial. The wells were washed twice with PBS and the supernatants were combined with the other supernatants. The cells were pelleted by centrifugation for 10 min. at 800×g. The cells were kept on ice until the immune fluorescence staining. The pellet was optionally resuspended in PBS.

Cultivation of T-Cells

The T-cells were isolated from 4-5 week old rabbits. The cells were centrifuged and immediately cultivated or frozen in aliquots of $3 \times 10^7$ cells. The thymocytes were seeded with a minimum cell density of $5 \times 10^5$ cells/ml of EL-4 B5 medium in 175 cm$^2$ culture flasks and incubated for 48 hours at 37° C.

Cultivation of Macrophages

Blood mononuclear cells from rabbits were cultivated in EL-4 B5 medium at a cell density of at least $1 \times 10^5$ cells/ml in 175 cm$^2$ culture flasks for 1.5 hours at 37° C. Afterwards the medium was removed and non-attached cells were removed from the attached macrophages by washing with warm EL-4 B5 medium, followed by cultivation for 48 hours in 35 ml medium.

Co-Cultivation of T-Cells and Macrophages

T-cells and macrophages were cultivated for 48 hours in separate flasks. Prior to combining both cell populations, the T-cells were centrifuged for 10 min. at 800×g. The supernatant was discarded and the cell pellet was resuspended in 10 ml medium. The T-cells were adjusted to a minimal cell density of $5 \times 10^5$ cells/ml and 10 pg phorbol-12-myristate-13-acetate (PMA) and 5 ng or 50 ng Phytohemagglutinin M (PHA-M) per ml of medium were added. The cultivation medium was removed from macrophages and the T-cell suspension was added to the flasks containing macrophages. After 36 hours of co-cultivation, the cultivation medium was removed and was termed TSN solution. For removal of remaining cells the TSN solution was filtered through a 0.22 µm filter. The TSN solution was frozen at −80° C. in aliquots of 4 ml.

Immunofluorescence Staining

Protocol 1:

Depending on the number of cells to be stained the cells were provided in 100 µl medium (less than $10^6$ cells) or 200 µl medium (more than $10^6$ cells), respectively. The fluorescent labeled antibody was diluted with 5% serum of the experimental animal and FACS buffer to a final volume of 100 µl or 200 µl, respectively. The reaction mixture was incubated on a roller rack for 40 min. at 4° C. in the dark. After the incubation the cells were washed twice at 300×g for 5 min. The pellet was resuspended in 400 µl PBS and filtered through a 70 µm sieve. The filtered solution was transferred to a FACS-vial and directly before the FACS experiment dead cells were stained by addition of propidium iodide (6.25 µg/ml). If the antibody was conjugated to biotin the antibody was detected in a second step with streptavidin labeled fluorophore (e.g. Alexa Flour® 647 (antibody 197)).

Protocol 2:

Anti-rabbit IgG FITC used for single cell sorting was from AbD Serotec (STAR121F, Düsseldorf, Germany).

For surface staining, cells were incubated with the optimally diluted anti-rabbit IgG FITC antibody in PBS for 30 min. with rolling at 4° C. in the dark. Following centrifugation, the supernatants were removed by aspiration. The PBMCs were subjected to two cycles of centrifugation and washing with ice cold PBS. Finally the PBMCs were resuspended in ice cold PBS and immediately subjected to the FACS analyses. Propidium iodide in a concentration of 5 µg/ml (BD Pharmingen, San Diego, CA, USA) was added prior to the FACS analyses to discriminate between dead and live cells. In other experiments the stained cells were single deposited by FACS.

A Becton Dickinson FACSAria equipped with a computer and the FACSDiva software (BD Biosciences, USA) were used to collect and analyze the data.

Proliferation Assays a) Cell Titer Glo (CTG) Viability Assay

The CTG viability assay (Promega; # G7571) was used according to the instructions of the manufacturer.

b) $^3$H Thymidine Assay

After 6 days of incubation $^3$H-Thymidin was added (0.5 µCi/well) and incubated for further 16 hours. The incorporation of $^3$H-Thymidine during cell proliferation was determined with a microplate scintillation counter (Wallac).

c) Microscopic Analysis

For the acquisition of microscopic images, a phase contrast microscope from Leica (Leica DM IL) combined with a high resolution camera (Leica DFC290 HD) was used.

d) Analysis of B-Cell Activation Via CFSE-Labeling.

Isolated B-cells were washed with sterile phosphate buffer saline solution (PBS). Up to $1 \times 10^7$ cells were resuspended in 1 ml protein-free PBS and incubated with CFSE (# C34554, Invitrogen/Molecular Probes) for 3 to 10 minutes at a final concentration of 2.5 µM at 37° C. CFSE loading was stopped by addition of an excess of FCS-supplemented medium. After extensive washing with FCS-containing medium, B-cells were used in co-culture experiments. Proliferation of CD19$^+$ gated (B−) cells as a consequence of CFSE dilution was confirmed by flow cytometric analysis (FL-1 channel) after indicated time points.

Quantification of IgG

Generally, the 96-well multi well plate in which the co-cultivation was performed was centrifuged after seven days of co-cultivation at 300×g for 5 min. 150 µl supernatant was removed and diluted at a ratio of 2:1 with PBS in a second 96-well multi well plate. The antibody was used at a concentration of 50 ng/ml. If the OD was or exceeded 1 after an incubation time of 5 min. a dilution series of from 0.8 to 108 ng/ml IgG was tested.

Specifically, a mixture of 0.5 µg/ml of biotinylated mouse anti-rabbit IgG antibody (Sigma-Aldrich) and 0.35 µg/ml anti-rabbit IgG HRP conjugate (Sigma-Aldrich) was transferred to 384 well streptavidin coated microtiter plates (MicroCoat Biotechnologie GmbH). Dilutions of B-cell supernatants in PBS supplemented with 0.5% BSA and 0.05% Tween®-20 were added and incubated for 90 min at RT. After repeated washing (6×) with PBST (phosphate buffered saline with 0.2% Tween®-20) buffer the plates were developed with BM Blue® HRP substrate solution and color formation was measured by absorbance at 370 nm. A commercial rabbit IgG (Sigma-Aldrich) was used as a calibration standard.

Detection of Antigen-Specific IgG

Generally, antibodies produced by single deposited and co-cultivated B-cells or from B-cells obtained from an immunized experimental animal can be characterized with respect to specific antigen binding. The ELISA was performed at room temperature and the ELISA-solution was incubated between the individual steps on a shaker at 20×g. In the first step the antigen was bound to the wells of a 96-well multi well plate. If the antigen was a protein it had been diluted in coating buffer and applied directly to the plate. Peptide antigens were bound via the specific binding pair biotin/streptavidin. The wells of the multi well plate can be already coated with soluble CroteinC (CrC) by the manufacturer. If not, the wells were incubated after the immobilization of the antigen with 200 µl blocking buffer. After the incubation with 100 µl antigen solution per well (pre-coated multi well plate) or 200 µl blocking buffer, respectively, non-bound antigen or blocking buffer was removed by washing with wash buffer. The diluted B-cell supernatants were added in a volume of 100 μl per well and incubated. After the incubation the wells were washed. Afterwards the detection antibody was added in a volume of 100 μl per well. The antibody can be either conjugated to horseradish peroxidase or labeled with biotin. The detection antibody was determined with a streptavidin-horseradish peroxidase conjugate. After the incubation the multi well plate was washed and afterwards 50 μl of a substrate solution containing 3,3',5,5' tetramethyl benzidine (TMB) were added per well and incubated for a period as given in Table X. The enzymatic reaction was stopped by the addition of 50 μl sulfuric acid and the optical density was determined at 450 nm and 680 nm with a photometer (Rainbow Thermo ELISA Reader) and the Xread plus-software.

Specifically, the assay was performed at room temperature (RT) on 384-well Maxisorp microtiter plates (Thermo Scientific) with PBS (phosphate buffered saline) buffer supplemented with 0.5% Gelatine and 0.025% Tween V-20. The plates were coated with 0.5 μg/ml of human serum albumin (HSA, Sigma-Aldrich) for at least 2 hours to overnight. After washing (3×) with PBST (PBS with 0.1% Tween®-20) buffer the wells were blocked with PBS with 0.5% Gelatine and 0.1% Tween®-20. Again, the plates were washed 3× and afterwards dilutions of B-cell supernatants were added. After an incubation of 60 min and 3 washing steps with PBST a 1:4000 dilution of a HRP-conjugated anti-rabbit IgG antibody (Amersham) was transferred to the wells and incubated for 60 min. Finally, the plates were repeatedly washed (6×) with PBST and developed with BM Blue® HRP substrate solution for 30 min. Absorbance was measured at 392-405 nm.

Panning on Antigen a) Coating of Plates

Biotin/Streptavidin: Sterile streptavidin-coated 6-well plates (cell culture grade) were incubated with biotinylated antigen at a concentration of 0.5-1(2) μg/ml in PBS at room temperature for one hour. Plates were washed in sterile PBS three times before use.

Covalently bound protein: Sterile cell culture 6-well plates were coated with 2 μg/ml protein in carbonate buffer (0.1 M sodium bicarbonate, 34 mM disodium hydrogen carbonate, pH 9.55) over night at 4° C. Plates were washed in sterile PBS three times before use.

b) Panning of B-cells on Peptides 6-well tissue culture plates coated with the respective antigen were seeded with up to $6\times10^6$ cells per 4 ml medium and allowed to bind for one hour at 37° C. in the incubator. Non-adherent cells were removed by carefully washing the wells 1-2 times with 1×PBS. The remaining sticky cells were detached by trypsin for 10 min. at 37° C. in the incubator and then washed twice in media. The cells were kept on ice until the immune fluorescence staining.

Example 1

Cultivation of EL-4 B5 Cells

The frozen EL-4 B5 cells were thawed rapidly in a water bath at 37° C., and diluted with 10 ml EL-4 B5 medium. After centrifugation at 300×g for 10 minutes the supernatant was discarded and the pellet resuspended in 1 ml medium.

The EL-4 B5 cells were inoculated at a cell density of $8\times10$ cells/ml in T175 cultivation flasks. Cell density was determined every second day and adjusted to $8\times10^4$ cells/mi. The cells have a doubling time of approximately 18 hours.

Cells were harvested and adjusted to a cell density of $1\times10^6$ cells/ml before γ-irradiation at 50 Gy.

Example 2

Co-Cultivation of B-Cells and EL-4 B5 Cells

Single cell sorted B-cells were cultured in 96-well plates with 200 μl/well EL-4 B5 medium with Pansorbin Cells (SAC) (Calbiochem (Merck), Darmstadt, Deutschland), EL-4 B5 cells ($5\times10^4$/well) and rabbit thymocyte supernatant (TSN) or cytokine mix (CM) with PMA, respectively, for 7 days at 37° C. in an atmosphere of 5% $CO_2$ in the incubator. B-cell culture supernatants were removed for screening and the cells harvested immediately for variable region gene cloning or frozen at −80° C. in 100 μl RLT buffer (Qiagen, Hilden, Germany).

What is claimed is:

1. A method for co-cultivating a single peripheral blood B-cell for production of an antibody, wherein said B cell is deposited into a well of a multi-well plate using fluorescence activated cell sorting (FACS) comprising the steps of:

a) supplementing a co-cultivation medium with a feeder mix, the feeder mix consisting of additives promoting the activation or survival of B cells or antibody secretion, wherein the co-cultivation medium supplemented with the feeder mix contains no other additives promoting the activation or survival of B cells or antibody secretion but those of feeder mix; and b) co-cultivating the B-cell with feeder cells in the presence of the co-cultivation medium supplemented with the feeder mix, wherein neither of a thymocyte cultivation supernatant, a macrophage cultivation supernatant, or a T-cell cultivation supernatant is added to the co-cultivation medium supplemented with the feeder mix, wherein the final concentration of the additives promoting the activation or survival of B cells or antibody secretion in the co-cultivation medium supplemented with the feeder mix is:

0.05-0.35 ng/ml phorbol myristate acetate (PMA), 0.02-0.2 ng/ml IL-1beta, 0.02-0.2 ng/ml TNFalpha, 0.5-5 ng/ml IL-2, 0.1-1 ng/ml IL-10, 0.1-1 ng/ml IL-6; and wherein said B-cell produces an antibody.

2. The method according to claim 1, wherein the final concentration of the additives promoting the activation or survival of B cells or antibody secretion in the co-cultivation medium supplemented with the feeder mix is:

0.05-0.35 ng/ml phorbol myristate acetate, 0.2 ng/ml IL-1beta, 0.2 ng/ml TNFalpha, 5 ng/ml IL-2, 1 ng/ml IL-10, and 1 ng/ml IL-6.

3. The method according to claim 1, wherein the final concentration of the additives promoting the activation or survival of B cells or antibody secretion in the co-cultivation medium supplemented with the feeder mix is:

0.2-0.35 ng/ml phorbol myristate acetate, 0.064 ng/ml IL-1beta, 0.064 ng/ml TNFalpha, 1.6 ng/ml IL-2, 0.32 ng/ml IL-10, and 0.32 ng/ml IL-6.

4. The method according to claim 1, wherein the final concentration of the additives promoting the activation or survival of B cells or antibody secretion in the co-cultivation medium supplemented with the feeder mix is:

0.05-0.2 ng/ml phorbol myristate acetate, 0.064 ng/ml IL-1beta, 0.064 ng/ml TNFalpha, 1.6 ng/ml IL-2, 0.32 ng/ml IL-10, and 0.32 ng/ml IL-6.

5. The method according to claim 1, wherein the IL-1beta has an activity of $5.5\text{-}14\times10^8$ IU/mg, the TNFalpha has an activity of $2.3\text{-}2.9\times10^8$ U/mg, the IL-2 has an activity of $6\text{-}7\times10^6$ IU/mg, the IL-10 has an activity of $6\text{-}7.5\times10^5$ IU/mg, and the IL-6 has an activity of $9.2\text{-}16.1\times10^8$ U/mg.

6. The method according to claim 1, wherein the feeder cells are EL4-B5 cells.

7. A method for producing an antibody comprising the co-cultivation method according to claim 1.

8. The method according to claim 3, wherein the feeder cells are EL4-B5 cells.

9. A method for producing an antibody comprising the co-cultivation method according to claim 2.

10. The method according to claim 4, wherein the feeder cells are EL4-B5 cells.

11. The method according to claim 5, wherein the feeder cells are EL4-B5 cells.

12. The method according to claim 1, where in the co-cultivation medium comprises RPMI 1640 medium supplemented with 10% (v/v) FCS, 1% (w/v) of 200 mM glutamine solution comprising penicillin and streptomycin, 2% (v/v) of 100 mM sodium pyruvate solution, and 1% (v/v) of a 1 M HEPES buffer.

13. The method according to claim 12, wherein the co-cultivation medium further comprises 0.05 mM beta-mercaptoethanol.

* * * * *